(12) United States Patent
Blackburn

(10) Patent No.: US 9,870,450 B2
(45) Date of Patent: Jan. 16, 2018

(54) DRUG DELIVERY REGULATOR

(71) Applicant: Zolo Solutions, Inc., Las Vegas, NV (US)

(72) Inventor: Christopher Blackburn, Las Vegas, NV (US)

(73) Assignee: Zolo Solutions, Inc., Las Vegas, NV (US)

( * ) Notice: Subject to any disclaimer, the term of this patent is extended or adjusted under 35 U.S.C. 154(b) by 343 days.

(21) Appl. No.: 13/934,845

(22) Filed: Jul. 3, 2013

(65) Prior Publication Data
US 2014/0074283 A1    Mar. 13, 2014

Related U.S. Application Data

(60) Provisional application No. 61/699,516, filed on Sep. 11, 2012.

(51) Int. Cl.
*G06F 19/00*    (2011.01)
*A61J 7/00*    (2006.01)
*A61J 1/03*    (2006.01)

(52) U.S. Cl.
CPC ........ *G06F 19/3462* (2013.01); *A61J 7/0076* (2013.01); *A61J 1/03* (2013.01); *A61J 2200/30* (2013.01)

(58) Field of Classification Search
CPC ........ A61J 2200/30; A61J 1/03; A61J 7/0076; G06F 19/3462
See application file for complete search history.

(56) References Cited

U.S. PATENT DOCUMENTS

| | | |
|---|---|---|
| 3,369,697 A | 2/1968 | Glucksman et al. |
| 3,998,356 A | 12/1976 | Christensen |
| 4,292,115 A | 9/1981 | Jones et al. |
| 4,293,845 A | 10/1981 | Villa-Real |
| 4,361,408 A | 11/1982 | Wirtschafter |
| 4,419,016 A | 12/1983 | Zoltan |
| 4,483,626 A | 11/1984 | Noble |
| 4,504,153 A | 3/1985 | Schollmeyer et al. |
| 4,572,403 A | 2/1986 | Benaroya |
| 4,573,606 A | 3/1986 | Lewis et al. |
| 4,589,780 A | 5/1986 | Takebe |
| 4,653,668 A * | 3/1987 | Gibilisco ........... B65D 83/0409 206/540 |

(Continued)

FOREIGN PATENT DOCUMENTS

WO    WO2010/066456    6/2010

OTHER PUBLICATIONS

Application No. PCT/US2013/58861, International Search Report and the Written Opinion of the International Searching Authority, or the Declaration dated Feb. 19, 2014. 14 pages.

(Continued)

*Primary Examiner* — Patrick Cicchino
(74) *Attorney, Agent, or Firm* — Ray Quinney & Nebeker, P.C.; Paul N. Taylor

(57) ABSTRACT

An apparatus for receiving, dispensing, and regulating controlled substances is provided. Furthermore the apparatus may comprise a portable, handheld container which is tamper-resistant and can withstand severe physical manipulation. The apparatus may only permit the dispensing of medication according to a prescribed schedule and dosage.

29 Claims, 9 Drawing Sheets

(56) References Cited

U.S. PATENT DOCUMENTS

| | | | |
|---|---|---|---|
| 4,674,651 A | 6/1987 | Scidmore et al. | |
| 4,674,652 A | 6/1987 | Aten et al. | |
| 4,695,954 A | 9/1987 | Rose et al. | |
| 4,717,008 A | 1/1988 | Ellison et al. | |
| 4,725,997 A | 2/1988 | Urquhart et al. | |
| 4,872,591 A | 10/1989 | Konopka | |
| 4,971,221 A | 11/1990 | Urquhart et al. | |
| 5,036,462 A | 7/1991 | Kaufman et al. | |
| 5,084,828 A | 1/1992 | Kaufman et al. | |
| 5,102,008 A | 4/1992 | Kaufman et al. | |
| 5,110,008 A * | 5/1992 | Moulding, Jr. | A61J 7/0076 221/15 |
| 5,126,957 A | 6/1992 | Kaufman et al. | |
| 5,142,484 A | 8/1992 | Kaufman et al. | |
| 5,148,944 A | 9/1992 | Kaufman et al. | |
| 5,197,632 A | 3/1993 | Kaufman et al. | |
| 5,219,093 A * | 6/1993 | Moulding, Jr. | A61J 7/0076 221/259 |
| 5,221,024 A | 6/1993 | Campbell | |
| 5,230,441 A | 7/1993 | Kaufman et al. | |
| 5,335,816 A | 8/1994 | Kaufman et al. | |
| 5,392,952 A | 2/1995 | Bowden | |
| 5,543,063 A | 8/1996 | Walker et al. | |
| 5,611,456 A | 3/1997 | Kasper | |
| 5,647,507 A | 7/1997 | Kasper | |
| 5,710,551 A | 1/1998 | Ridgeway | |
| 6,018,289 A | 1/2000 | Sekura | |
| 6,108,588 A | 8/2000 | McGrady | |
| 6,163,737 A | 12/2000 | Fedor et al. | |
| 6,198,383 B1 | 3/2001 | Sekura | |
| 6,594,549 B2 | 7/2003 | Siegel | |
| 6,973,371 B1 | 12/2005 | Benouali | |
| 6,985,869 B1 | 1/2006 | Stoll et al. | |
| 7,002,476 B2 | 2/2006 | Rapchack | |
| 7,048,141 B2 * | 5/2006 | Abdulhay | G07F 11/10 221/15 |
| 7,330,101 B2 | 2/2008 | Sekura | |
| 7,359,765 B2 * | 4/2008 | Varvarelis | A61J 7/0481 221/265 |
| 7,454,267 B2 | 11/2008 | Bonney et al. | |
| 7,711,449 B2 | 5/2010 | Abdulhay et al. | |
| 7,715,277 B2 | 5/2010 | De La Huerga | |
| 7,720,569 B2 | 5/2010 | Forrester et al. | |
| 7,743,923 B2 | 6/2010 | Conley | |
| 7,751,932 B1 | 7/2010 | Fedor | |
| 7,882,980 B1 | 2/2011 | Horn | |
| 7,885,725 B2 | 2/2011 | Dunn | |
| 7,896,192 B2 | 3/2011 | Conley et al. | |
| 7,944,342 B2 | 5/2011 | Sekura | |
| 7,978,564 B2 | 7/2011 | De La Huerga | |
| 7,996,106 B2 * | 8/2011 | Ervin | G06F 19/3462 700/237 |
| 8,068,934 B2 * | 11/2011 | Saltsov | A61J 7/0084 221/121 |
| 8,180,485 B2 | 5/2012 | Rickelhoff | |
| 8,666,539 B2 * | 3/2014 | Ervin | A61J 1/03 700/236 |
| 8,752,728 B2 * | 6/2014 | Tignanelli | A61J 1/03 221/15 |
| 8,818,820 B1 | 8/2014 | Mehdizadeh | |
| 9,014,427 B2 | 4/2015 | Bear et al. | |
| 9,014,847 B2 * | 4/2015 | Dunn | G06F 19/3462 700/236 |
| 9,542,534 B1 | 1/2017 | Ducatt | |
| 9,572,748 B2 | 2/2017 | Lim et al. | |
| 2003/0183642 A1 * | 10/2003 | Kempker, Sr. | A61J 7/0084 221/2 |
| 2004/0019794 A1 | 1/2004 | Moradi et al. | |
| 2005/0096628 A1 | 5/2005 | Greeven et al. | |
| 2006/0071011 A1 * | 4/2006 | Varvarelis | A61J 7/0481 221/9 |
| 2007/0012712 A1 | 1/2007 | Syiau | |
| 2008/0054007 A1 | 3/2008 | Mador | |
| 2009/0294521 A1 | 12/2009 | De La Huerga | |
| 2010/0004772 A1 * | 1/2010 | Elfstrom | G06Q 10/06 700/103 |
| 2010/0030374 A1 * | 2/2010 | Saltsov | A61J 7/0084 700/225 |
| 2010/0258565 A1 * | 10/2010 | Isaacson | B09B 3/0075 220/324 |
| 2011/0172812 A1 | 7/2011 | Joslyn | |
| 2012/0006700 A1 * | 1/2012 | Geboers | A61J 7/0084 206/216 |
| 2012/0046970 A1 | 2/2012 | Potts | |
| 2013/0226339 A1 * | 8/2013 | Ervin | G07F 17/0092 700/240 |
| 2014/0074283 A1 * | 3/2014 | Blackburn | A61J 7/0076 700/237 |
| 2014/0074505 A1 | 3/2014 | Scanlon | |
| 2014/0262918 A1 * | 9/2014 | Chu | A61J 1/03 206/534 |
| 2014/0339248 A1 * | 11/2014 | Reddy | A61J 7/0076 221/1 |
| 2014/0346184 A1 | 11/2014 | Bae et al. | |
| 2015/0081330 A1 | 3/2015 | Mann et al. | |
| 2015/0259110 A1 * | 9/2015 | Blackburn | B65D 50/00 222/1 |
| 2015/0272825 A1 | 10/2015 | Lim et al. | |
| 2015/0359711 A1 | 12/2015 | Ducatt et al. | |

OTHER PUBLICATIONS

Anonymous: "Ultimate tensile strength", Wikipedia, Jul. 11, 2013, XP055265025, Retrieved from: https://en.wikipedia.org/w/index.php?title=Ultimate_tensile_strength&oldid=501787147; Retrieved Apr. 13, 2016, 6 pages.

Anonymous: "Strength—Toughness", XP055265035, Cambridge, UK, Retrieved from: http://www.materials.eng.cam.ac.uk/mpsite/interactive_charts/strength-toughness/basic.html; Retrieved Apr. 13, 2016, 6 pages.

Anonymous: "Strength of materials", Wikipedia Sep. 7, 2012, XP055264821, Retrieved from: http://en.wikipedia.org/w/index.php?title=Strength_of_materials&oldid=511296893; Retrieved Apr. 12, 2016, 7 pages.

Anonymous: "Toughness", Wikipedia, Jul. 8, 2012, XP055264818, Retrieved from: http://en.wikipedia.org/w/index.php?title=Toughness&oldid=501306911; Retrieved Apr. 12, 2016, 2 pages.

U.S. Appl. No. 14/725,969, dated Jun. 27, 2017, Office Action.
U.S. Appl. No. 14/725,969, dated Oct. 5, 2017, Office Action.

* cited by examiner

DRUG DELIVERY REGULATOR

CROSS REFERENCE TO RELATED APPLICATION

This application claims priority to U.S. Provisional Application No. 61/699,516 filed Sep. 11, 2012, which is incorporated herein in its entirety.

FIELD OF TECHNOLOGY

The following relates to an apparatus for dispensing a restricted substance such as prescribed medications and a method for the secure dispensation thereof. More specifically, the following relates to embodiments of an apparatus comprising a portable container which is tamper-resistant and can withstand severe physical manipulation. Furthermore, the container will only permit the dispensing of a substance according to a prescribed dosing schedule.

BACKGROUND

The field of prescription medications is replete with dangerous, highly addictive, and potentially lethal drugs which, if not properly dosed, regulated and administered are susceptible to misuse, abuse, overdoses and toxicity which may or may not be intentional. In some situations improper dosing or an improper combination of medications may even result in death. The presence and accessibility to these medications in millions of homes presents a potentially significant safety risk to patients and other individuals who may come in contact with these medications. Drug poisoning is the second leading cause of injury-related deaths, accounting for 22,134 deaths in the United States according to a study published in 2013. Some of these deaths are the result of intentional overdose while others are the result of unintentional lethal combinations or doses of prescription medications. These overdose cases cost insurance companies approximately $72.5 billion in health care expenses each year.

Patients may also forget the appropriate schedule for taking their medication. Often, a patient may become confused or may have difficulty remembering whether or not they have taken their medication for the day, what dose they were supposed to take and whether or not the patient has individualized instructions.

Additionally, many medications, such as narcotics including opiates and their derivatives, central nervous system depressants such as benzodiazepines and stimulants such as Adderall are susceptible to abuse or black market transfers. A patient may become addicted to a controlled substance and attempt to take more than the appropriate dose prescribed by a healthcare professional or authorized individual capable of prescribing the substance. In other instances, a patient may attempt to sell controlled substances, which are only available through a prescription, to a non-prescribed individual or a non-prescribed individual may attempt to surreptitiously take drugs for themselves. Prescribed medications if not taken properly, or if taken by someone other than the prescribed patient, could result in serious physiological damage, psychological impairment and even death. Due to the vast number of prescriptions that are filled annually and the rising potential for drug abuse, there is a clear need for better medication security. Thus, a need exists for an apparatus, and a method for securely dispensing medications and other controlled substances according to a prescribed schedule and dosage using a portable, handheld container which is tamper-resistant and can withstand severe physical manipulation.

BRIEF SUMMARY OF THE INVENTION

A first general aspect relates to a tamper-resistant drug receiving, regulating and dispensing apparatus comprising: a tamper-resistant canister constructed of a durable break-resistant material, the tamper-resistant canister comprising at least one access compartment, at least one regulating unit, and a locking mechanism; a controller operably in communication with the locking mechanism, the controller configured to at least control the locking mechanism; and a communication component operably in communication with the controller, the communication component configured to communicate with a device external to the tamper-resistant drug receiving, regulating and dispensing apparatus.

A second general aspect relates to a method for securing and controlling the dispersion of drugs contained in a tamper-resistant apparatus, the method comprising the steps of: providing a tamper-resistant apparatus having a removable cover, a controller, and a body having a portion thereof configured to receive and retain drugs; engaging a locking mechanism to prevent the separation of the apparatus cover from the apparatus body; programming the controller with a security input to control the operation of the locking mechanism; programming the controller to facilitate dispersion of the contents of the apparatus body at a controlled rate; and communicating activity of the apparatus body to an external administrative user.

A third general aspect relates to an apparatus for securely dispensing drugs contained at a controlled rate, the apparatus comprising: a tamper-resistant canister, wherein the tamper-resistant canister is comprised of at least two portions, the at least two portions being movable with respect to each other to facilitate access within the canister; a communications component, within the tamper-resistant canister, the communications component configured to receive data from a source external to the tamper-resistant canister; a control unit, within the tamper-resistant canister, the control unit configured to process data received from, at least, the communications component; a locking mechanism in operable communication with the control unit, the locking mechanism configured to lock the two movable portions of the tamper-resistant canister and prevent unwanted movement of the two movable portions of the tamper-resistant canister; an access compartment configured to facilitate reception of drugs within the tamper-resistant canister, when the compartment is accessed via operation of the locking mechanism to permit controlled movement of the two movable portions of the tamper-resistant canister and facilitate access into the tamper-resistant canister; a regulating unit in operable communication with the access compartment, the regulating unit configured to regulate the size or amount of drugs to be dispensed; and a dispensing unit in operable communication with the regulating unit, the dispensing unit configured to dispense the regulated drugs according to data provided by an external source and processed by the control unit.

The foregoing and other features of construction and operation will be more readily understood and fully appreciated from the following detailed disclosure, taken in conjunction with accompanying drawings.

BRIEF DESCRIPTION OF THE DRAWINGS

Some of the embodiments will be described in detail, with reference to the following figures, wherein like designations denote like members, wherein.

DETAILED DESCRIPTION

A detailed description of the hereinafter described embodiments of the disclosed apparatus, method, and system are presented herein by way of exemplification and not limitation with reference to the Figures. Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure.

As a preface to the detailed description, it should be noted that, as used in this specification and the appended claims, the singular forms "a", "an" and "the" include plural referents, unless the context clearly dictates otherwise.

Figure 1:
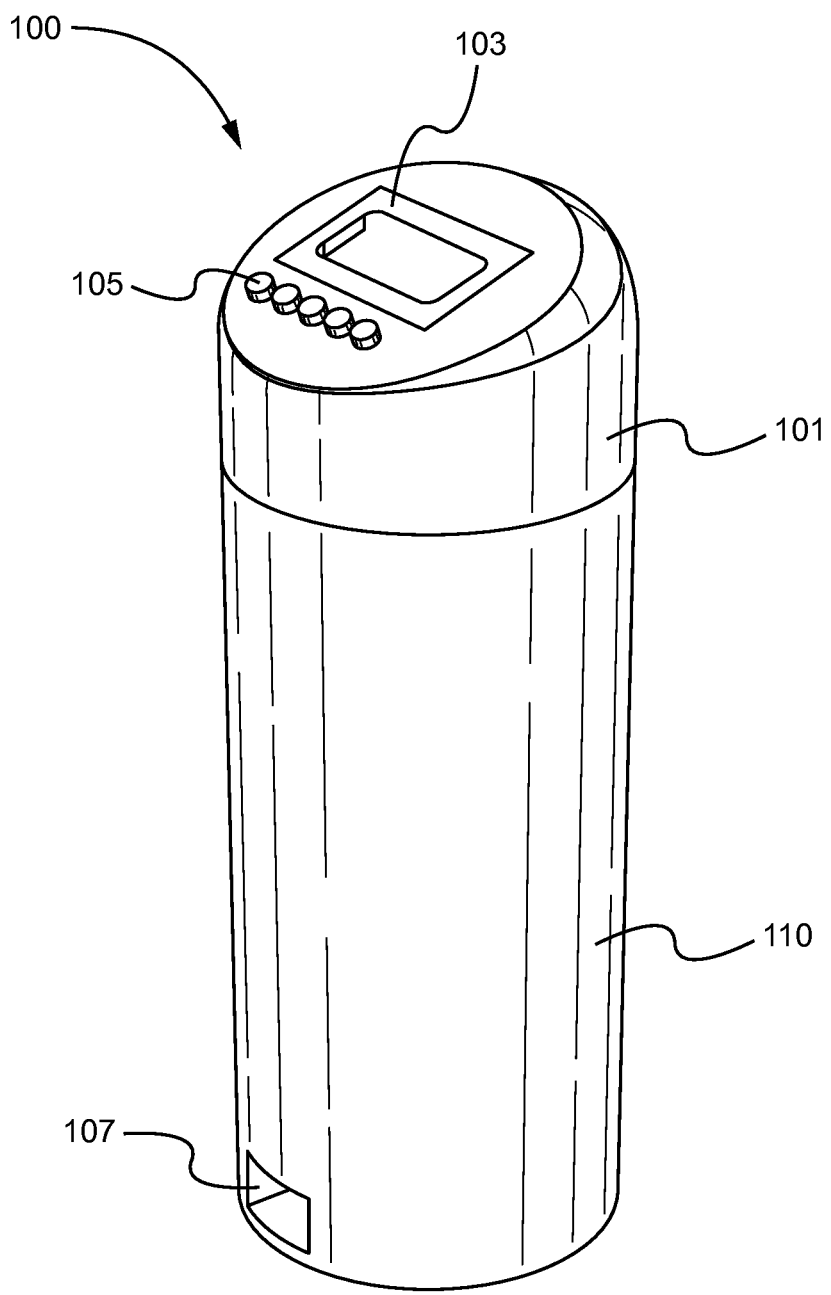
FIG. 1 depicts an embodiment of an apparatus for receiving, dispensing, and regulating a controlled substance.

Referring to the drawings, FIG. 1 depicts an embodiment of a tamper-proof, tamper-resistant drug-delivery and regulating apparatus 100 for receiving, regulating, and dispensing contents stored within, including as an example a controlled substance. Embodiments of a drug delivery and regulating apparatus 100 may include a tamper-resistant body 110 and a tamper-resistant cover 101, constructed of a break-resistant material or a shatter resistant material. The tamper-resistant apparatus may be any size, shape volume or weight. In the exemplary embodiment, the apparatus 100 may be lightweight and easy to hold. For example, in some embodiments, the apparatus may include outer dimensions similar to a water bottle. In one embodiment, the apparatus may weigh between one kg and 300 g. In another embodiment, the apparatus may weigh as little as 85 g. In yet additional alternative embodiments, the apparatus may be much larger. The apparatus may also be designed in various shapes as well. In some embodiments, the apparatus may be square, rounded or cylindrical. In alternative embodiments, the device may include a round cover 101 and a flat bottom so that the apparatus may stand freely in the proper orientation. In an alternative embodiment, the apparatus may be designed or ergonomically shaped to include features and operation mechanisms for people with disabilities or limited mobility and dexterity.

The durable and break-resistant or shatter resistant material which the apparatus 100 may be constructed from may include any material that is capable of withstanding severe physical impacts, cutting apparatuses, firearms, and extreme temperatures. Such materials may include impact resistant plastics, resins, nylon, metals, rubbers, polymers, polyresins, alloys, carbon fiber, acrylic, polycarbonate, polyester, PET, PETG, Kevlar, Lexan, carbon fiber composites, Nalgene®, Acrylite®, Duraplex®, Hygard®, Makrolon®, Micarta®, Nylatron®, other similar materials or a combination thereof.

Embodiments of a tamper-resistant apparatus may include a body 110 which prevents unauthorized access. Unauthorized access may include access by a person other than the intended recipient of the controlled substance, access by the intended recipient attempting to obtain the controlled substance for someone other than the intended recipient, or access by any person attempting to obtain an amount of the contents of the apparatus that is different from the prescribed or intended dosing schedule.

Tests were conducted to determine the component strength of significantly break-proof material utilized in forming a variation of an embodiment of the present invention. For example, researchers performed a battery of tests on polycarbonate tubing comprising a portion of a canister body, to ensure that it would be capable of withstanding the extreme forces that an end user may potentially exert on the apparatus in an unauthorized attempt to reach the contents of the interior. The testing involved a finite element analysis model with a force of 40,000 lbs. across the median of the apparatus.

During a first test of the substantially break-proof tamper-resistant body 110, a 12 inch section was struck 30 times by a professional welder. The tester used an 8 pound sledge hammer and was swinging as hard as possible. The material was visibly scarred with minor dimples but it remained structurally sound. The body did not crack or break, and retained its round shape, demonstrating the capability of the structure to prevent an individual from tampering with the apparatus using blunt force.

During a second test, a 6 inch section of the body was stepped on and bounced on repeatedly by a 180 pound researcher. The tube deformed to an oval shape, however it did not crack or break. In addition, the third test loaded the body vertically with 600 lbs. The weight had no effect on the body.

In a fourth structural test, the body 110 was driven over by a large truck. The truck was incapable of smashing the device. The results indicated that the body was deformed to an oval shape, but was neither cracked nor broken.

The testing on the polycarbonate embodiment demonstrated desirable strength, durability and robustness requirements in the performance characteristics of the device. While polycarbonate was the material tested, various materials may be adequate for the body and/or components of the apparatus 100. It may be desirable for some embodiments to have properties such as a tensile strength greater than 40 MPa, and impact strength greater than 5 ft-lb/in and a flexural strength greater than 59 MPa.

The body and the components may be injection molded out of polycarbonate, acrylonitrile butadiene styrene (abs), or an ABS-PC blend. However, the device may also be cut, turned, printed, welded, roto-molded, blow-molded, extruded, milled, stamped, forged, or otherwise formed. While a dispenser having a cylindrical shape may lend itself to having potential weak spots (resulting from a significant impact on the corners of the base, or a high cutting force may breach the device, the advantages of the shape may outweigh the disadvantages. Attempts to break into the device, by nature of the catastrophic damage to the device, may be further evidenced in the scars on the device.

Embodiments of a tamper-resistant body may include a body which is moisture tight vapor tight, and chemically inert to prevent attempts at disintegrating, dissolving, melting, or otherwise extracting the potentially lethal medications by various means other than the regimented and scheduled dosing. The design of the apparatus may prohibit extraneous liquids from entering the access compartment 130 or other content storage areas of the apparatus. The apparatus may contain security elements, locking mechanisms and features that may restrict children or unauthorized users from tampering with or extracting controlled substances. This feature may or may not be used as necessary.

Embodiments of the apparatus 100 may include an apparatus which is designed such that any attempt to forcefully extract controlled substances by any means other than as the apparatus is designed and programmed will require such extreme force as to result in catastrophic destruction of the apparatus. Use of the apparatus to dispense controlled substances may be available as the intended recipient travels. This apparatus may be portable and handheld in size to fit in a pocket, purse, briefcase, suitcase or any other such container. For this reason as well, the apparatus may be made of materials that will allow sufficient visibility with x-ray machines and may be designed to be in compliance with the regulations of the Transportation Security Agency (TSA). In some embodiments, the Apparatus 100 may include a volume between 800 to 1000 $cm^3$. The volume of the apparatus may further be reduced by using smaller components including smaller wheels 532, 533, motors 234a, 234b and electronics 405. Volume may also be reduced or enlarged depending on the size and the amount of contents which may need to be dispensed. For example, a larger solid dosage form may require an apparatus with an increased volume compared with a smaller solid dosage form.

The general cylindrical shape may be structurally sound to help inhibit physical tampering. The bottom of the device may be flat so that it can be set on flat surfaces. The top of the device may be rounded so that the only stable free-standing orientation is on the bottom. Orientation is important for the dispenser to properly function since in certain embodiments, the contents may depend on gravity to travel through the device.

Embodiments of the tamper-resistant apparatus 100 may further include an exit path 107. The exit path 107 may take any form that allows the receipt of the contents of the tamper-resistant apparatus by a user of the apparatus 100 without having to access or being unable to access, the interior portion of the apparatus 100. In one embodiment, the exit path 107 may be a slot or bore in the canister body. In an alternative embodiment, the exit path 107 may include a sliding drawer. In yet another alternative embodiment, a flip open cover, a door, hatch, cap, flap, lid, top, or closure may be opened to reveal the extruded contents of the apparatus.

The exit path may also prevent the user from inserting objects or other substances including fluids into the apparatus in an attempt to extract the remaining contents from the access compartment 130. The exit path 107 may include an access mechanism or plurality of access mechanisms. An access mechanism may include a door, hatch, cap, cover, flap, lid, top, closure, elevator or other mechanism which may be securely closed and opened by an administrative user or a feature that may limit inappropriate access to the dispensing unit 140 or regulating unit 230. Embodiments of an administrative user may include a doctor, nurse, pharmacist, physician's assistant, medical professional, veterinarian, or other individual who is authorized to fill the apparatus 100 with a substance. An authorized user may include a patient who may be allowed to access the contents of the apparatus at a prescribed point in time. An access mechanism may be permanently connected to the apparatus as in a door or a slide, or may be removable as in a screw cap or removable cover. Embodiments of an access mechanism may be waterproof, moisture-tight, and vapor-tight. In some embodiments, the apparatus 100 may be reused for the subsequent reloading of controlled substances at an approved facility such as a pharmacy for instances of dose or medicine changes or prescribed refills. In other embodiments, the apparatus may be disposable. Those skilled in the art should appreciate that there may be other embodiments of an access mechanism.

Embodiments of a tamper-resistant drug-delivery regulation apparatus 100 may receive, dispense, and regulate a controlled substance or a plurality of controlled substances. An apparatus 100 may have one or more access compartments 130 to receive, dispense, and regulate a controlled substance or a plurality of controlled substances. Furthermore, embodiments of the apparatus 100 may include an access compartment 130 or a plurality of dispensers that may receive, dispense, and regulate controlled substances in different dosage forms (i.e. a solid, a liquid, and a gas or vapor). For example, in one embodiment, a dispenser may receive, dispense, and regulate a controlled substance in liquid dosage form in a first compartment, and a controlled substance in a solid dosage form such as a pill in a second compartment, and a controlled substance in a gaseous form such as an inhalent in a third compartment.

The access compartment 130 may include a variable insert 331 or a series of inserts which may control the size and/or amount of the contents being dispensed. The insert 331 may be any solid or rigid material capable of restricting or expanding the entrance to the regulating device 230. For instance the variable insert 331 may attach to the side or center of the access compartment 130 and may further cover or restrict the size of the entrance to the regulating device 230. In one embodiment, the variable insert may include clip 580 or other mechanism which may attach along the access compartment. In order to accommodate a range of pill shapes and sizes, various inserts 331 can be interchanged in the dispenser. In some embodiments, the variable insert may have a ramped surface 582 which may cover or limit the entrance to the regulating device 230. The ramped surface 582 may be extendable or retractable to accommodate the various sizes of the contents stored in the access compartment. In an alternative embodiment, the power source enclosure 202 retaining wall may serve to support the power source and may also act as a variable insert to adjust the size of the gap between the regulating device.

The access compartment 130 may be any size or volume necessary to store the desired contents. For example, in some embodiments, the access compartment may be 120 $cm^3$ while in more portable embodiments, the access compartment may be half that size to allow for a more travel capable apparatus.

Embodiments of substances that may be loaded into the apparatus may include prescription medication, over the counter medication, dietary supplements, vitamins, minerals or any other substance which may be ingested or otherwise consumed or taken into the physical body of an individual. Embodiments of a controlled substance may include any drug whose manufacture, possession or use may be regulated by the government or a substance that is subject to legislative control or executive branch regulation. Controlled substances may include, but are not limited to any other class of drug classified by the US Food and Drug Administration. These classes may include narcotics such as opioids and their derivatives, antidepressants, psychotherapeutics, benzodiazepines, barbiturates, pain killers, and DEA scheduled drugs I-IV. A controlled substance may also include any substance which is prescribed by healthcare professional such as a physician, dentist, physical therapist, psychiatrist or any other profession capable of prescribing medications.

Dosage forms of a substance or a controlled substance which may be inserted into the apparatus 100 for dispensation may include an aerosol, bar, bead, block, pill, tablet, capsule, cloth, concentrate, cone, core, powder, cream, crystal, diaphragm, disc, dressing, elixir, emulsion, enema, extract, fiber, film, solution, suspension, solid, liquid, gas, gel, generator, globule, granule, gum, implant, inhalant, injectable, insert, intrauterine device, irrigant, jelly, liner, liniment, lipstick, lotion, shampoo, lozenge, mouthwash, oil, ointment, packing, paste, pastille, patch, pellet, pill, plaster, poultice, ring, rinse, salve, soap, sponge, spray, stick, suppository, suspension, syrup, chewable, effervescent, osmotic, tincture, troche, wafer, vapor, or any other formulation which may be administered to an intended recipient. Substances and controlled substances placed within the apparatus 100 may also be loaded with an included delivery method such as pre-filled syringes, inhalers or inhalant canisters or any other instruments used to administer substances to an intended recipient. The apparatus 100 may function to execute controlled substance delivery through either mechanical or electrical means, or a combination of both, to facilitate dispersion of a prescribed dosage at a determined interval for drug delivery.

Embodiments of the tamper-resistant apparatus may include an output device 103. The output device 103 may be any mechanism which is capable of communicating information to an individual in possession of the apparatus. In one embodiment, the output device 103 may include a visual display, screen or monitor. Examples of a the output device 103 may include cathode ray tubes (CRT), liquid crystal display (LCD), light emitting diodes (LED), organic light emitting diode (OLED), Digital Light Processing (DLP), plasma screen, touchscreen, holographic display, digital visual display, split-flap display, tell-tale, or any other display which may convey information. The output device may be constructed out of a break proof material or the output device 103 may further include a retractable or removable cover which may be constructed out of a break proof material.

Embodiments of an output display 103 may be able to display digits, alphanumeric characters, icons, images, pictures, photographs, videos, still or moving graphical representations, and/or other like visual depictions. Embodiments of a digital visual display may include a seven-segment display, a fourteen-segment display, or a sixteen-segment display, or may include any display depicting images at any known resolution. For example embodiments may include, but are not limited to, resolutions such as 640×480, 800× 600, 960×640, 1024×768, 1280×720 (720p), 1366×768, 1440×1080 (HDV 1080i), 1920×1080(1080p), 2048×1152 (2K), 4096×2304 (4K), 7680×4320 (4320p). Alternative embodiments of a display unit 103 may include a tactile display. Embodiments of a tactile display may include a refreshable Braille display, an Optacon®, or any other display which may convey information tactilely. The display may combine both tactile and visual functionality in congruent operation. Portions of, or the entirety of, the outer surface of the device may be configured for visual display. Those skilled in the art should appreciate that there may be other embodiments of a display unit.

The output device 103 may externally display information to users of the tamper-resistant apparatus 100. Information displayed may include the apparatus's identification number, a user ID number, prescribing health care professional information, the name of the contents within the apparatus such as a drug name, dosage strength, the quantity of the contents stored within the apparatus, the size of the contents stored within the apparatus, the expiration date of the contents, the dosing schedule or rate of content administration, a countdown timer until the next dose, administrative user contact information such as doctors, dentists, physical therapists, pharmacists, and nurses. Embodiments of recipients or users of apparatus 100 may include humans, animals such dogs, cats, pigs, horses, cows, sheep, any other mammal, fish, reptiles or any other genus or species which may benefit from the use of a controlled substance. Embodiments of intended recipients may include the person or animal who has been prescribed the controlled substance, or any individual who is authorized to receive the controlled substance on the recipient's behalf for the purpose of ensuring proper administration.

In one embodiment, displayed information may include a timer, clock or countdown which may guide the user when the apparatus 100 will administer the next dose. In another embodiment, the output device 103 may display patient information. Patient information may include the patient's name, age, sex, prescribed drugs, prescription history and allergies. In alternative embodiments, the output device 103 may include information about the drug including contraindications, side effects, drug interactions, dosing schedule, and dosing concentrations. Furthermore, additional embodiments may display additional dosing instructions, for example, the display may inform the patient to take the dose before or after a meal, or it may inform the patient to take with a full glass of water, or even inform the patient to allow a specific amount of time after dosing before performing certain activities. For example, the output 103 may display to the patient a warning not to drive a car or operate machinery for at least 5 hours after taking the prescribed dose. In another example, such as when the prescribed contents of the apparatus are sedatives or sleep aids, the output 103 may warn the patient to take a dosage before bed and may also inform the patient to allow for a certain number hours of sleep. In an alternative embodiment, multiple sets of patient information may be stored in a single apparatus 100. Display information may be sorted by a user number or may be accessed by inputting a password, passcode or another form of identifiable user input such as thumbprint, facial scan, retinal scan, biometric data, touch screen hand gestures or any other method which may be used to identify a specific individual. In some embodiments, the patient information and user input may be displayed directly on the display 103. In other embodiments, inputs of the user interface may be displayed on a prescribed individual's network enabled computing devices such as mobile computing device. For example, in one embodiment, the patient may input their required input into the user interface to dispense the contents wirelessly right from their mobile computing device.

Embodiments of apparatus 100 may also include an audio output. Embodiments of an audio output may include any device which creates an electrical or other representation of sound. An audio output may include a speaker, loudspeaker, computer speaker, multimedia speaker, driver, tweeter, electro-acoustic transducer, or any other device which may turn an electrical signal into a sound. The apparatus may also contain a reminder alarm that prompts intended recipients for a scheduled dosage of controlled substance. Those skilled in the art should appreciate that there may be other audio output embodiments.

Embodiments of the tamper-resistant apparatus may also communicate with devices external to the tamper-resistant apparatus. For instance, the apparatus may sync with a mobile computing device or other computing device loaded with an application in its memory for communicating with the apparatus 100. In one embodiment, the apparatus may communicate with an external device via a communication component, such as a through a cable connection port or via wireless transmission, to send information to the mobile device. Communications with external devices may also be facilitated through communication components such as input device 105 or the output 103, wherein the output may be user-interactive. For example, information communicated may include dosing reminders, refill reminders, and any other information that may also displayed on the output 103, and then confirmed via interaction with the output 103 or with the input device 105.

Embodiments of the tamper-resistant apparatus 100 may include a user interface 105. A user interface 105 may include any method or means for allowing a user external to the tamper-resistant apparatus 100 to interact with the apparatus, including programming or providing data, instructions, commands, and the like to the apparatus, or responding to the apparatus's request for information. In one embodiment, the user interface may include physical hardware that a user may use to interact with the apparatus such as push buttons, dials, switches, joysticks, keypads, keyboards, mice, trackball, swipe card readers, biometric analysis such as retinal scans, facial recognition, voice interface, thumbprint analysis and combinations of inputs thereof.

In an alternative embodiment, the user interface 105 may be incorporated into the output device 103. For example, the output device 103 may be an interactive touch screen or touch pad. The touch screen or touch pad may include surfaces which allow the user to touch, press, swipe and interact with the output device 103 in such a manner that the user may provide instructions or responses to the apparatus 100. In alternative embodiments, a touch screen may recognize simple gestures involving a single finger. In alternative embodiments, more complex gestures may be used such as a multi-touch gesture which may include multiple fingered gestures. A touch screen may be interacted with using a hand gestures or it may recognize inputs from a devices that touch the screen such as a stylus.

Embodiments of a user interface may include a secure user interface. For example, a user interface may be password-protected, or may incorporate biometric protection such as fingerprint or voice identification, or the input may require the use of a separate key or an RFID tag. Those skilled in the art should appreciate that there may be other embodiments of a user interface. In one embodiment, the user interface 105 may perform a gate keeping function. The user interface may control access to the interior of the apparatus body 110. In another embodiment, the user interface 105 may require input for access to patient information or to view information displayed on the output device 103. For example a user may be required to input a specific access code, combination of inputs, or secret gestures to display information. In an alternative embodiment, multiple users may have a different set of inputs which allows the apparatus to differentiate between users and to determine which information should be displayed.

The user interface 105 may also be at a separate location from the apparatus 100. The apparatus 100 may include a communication component in some embodiments. A communication component may be any device or method for sending and receiving signals or input data to and from an exterior origin outside of the apparatus 100. A communication component may be linked to external data sources either wirelessly or via wired communications. Communications between the device and other outside sources may be encrypted to prevent users from hacking or tampering with the apparatus in an attempt to thwart controlled drug delivery. Communications may be tagged with the Unique Device ID to help determine that the communications are properly effected. Embodiments of a communication component may include wireless transmitters, receivers, and/or transceivers, such as a BlueTooth®, Wi-Fi®, or other wireless transmitter, receiver, or an extraneously powered transceiver that can facilitate transfer of data between the apparatus and outside sources. Embodiments of a communication component may be integrated wirelessly or otherwise with a mobile communication device such as a mobile telephone. Furthermore, the communication component may also be wired. Such wired communication may be through a port, such as a USB®, micro-USB®, HDMI®, micro-HDMI® or other cable-based data transmitting component that is capable of uploading and/or downloading data to and from the memory of the apparatus. Those skilled in the art should appreciate that there may be other embodiments of a communication component.

In one embodiment the communication component may be transmitting and receiving data, with the controller, or control unit, for regulating the dispensation of contents of the apparatus. The controller or control unit may be attached or integrated with PCB 415. The apparatus 100 may be designed so that controlled substances cannot be obtained in any amount, at any time, or by any means other than what has been prescribed. The communication component may be wired, wireless or a combination thereof. For example, a communication component may be wireless network interface card (NIC), an USB port, Ethernet port, radio transmitter/receiver, Bluetooth transmitter/receiver, or infrared transmitter/receiver. In some embodiments, the communication component may be capable of networking the apparatus 100 to a computer network, while in other embodiments, the communications port may be used to transmit data to and from the apparatus. Embodiments of data transmitted to and from the apparatus may include information about the contents of the apparatus, the time that controlled substances were dispensed, the time that controlled substance was received, the amount of controlled substance remaining, information about refilling the apparatus, prescription information, contraindication information, attempts at unauthorized access to the apparatus, damage to the apparatus, or location of the apparatus. Those skilled in the art should appreciate that there may be other embodiments of data transmitted to and from the apparatus.

For example, in one embodiment, the communication component may network with an external computing device. The external computing device may send signals to the apparatus such as programming user information, validating user inputs, locking and unlocking apparatus. In another example, an administrative user such as a doctor or pharmacist may have a master program loaded on an external computing device which can communicate with the apparatus and program it.

Figure 2:
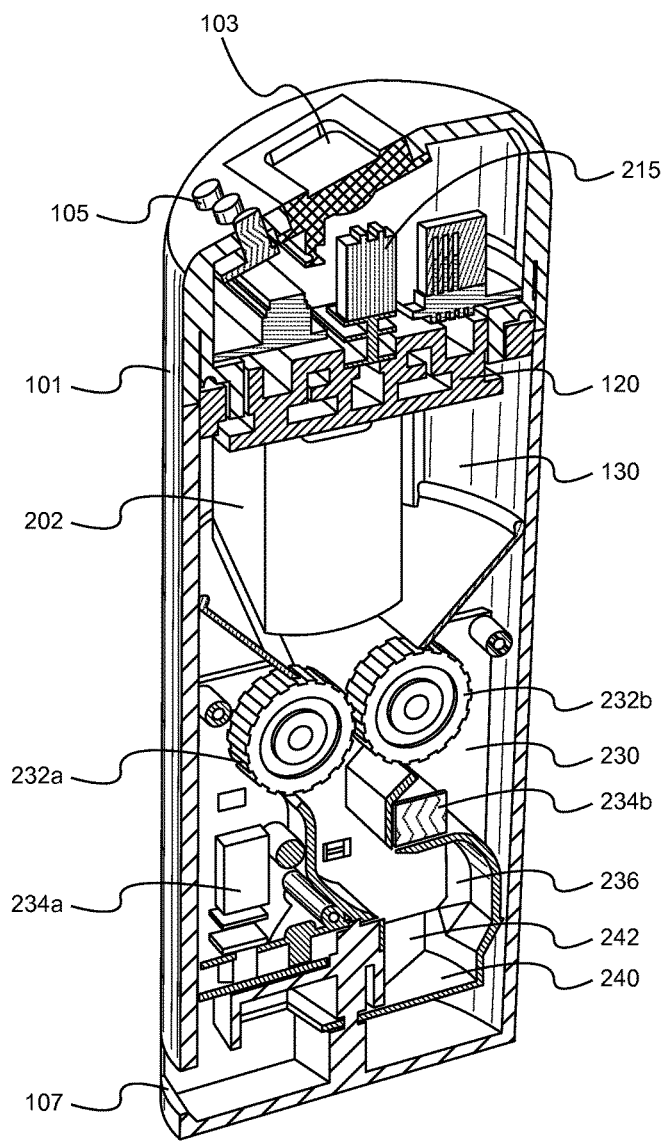
FIG. 2 depicts a cross section of the embodiment of an apparatus for receiving, dispensing, and regulating a controlled substance depicted in FIG. 1.

Referring to FIG. 2, which depicts cross sectional view of an embodiment of a tamper-resistant drug-delivery regulation apparatus 100 for receiving, dispensing, and regulating a controlled substance, the apparatus 100 may include a controller or control unit. A controller may be any device capable exerting control over various components of the apparatus such as the locking mechanism 120, a locking mechanism motor 215 may enable the separation of the tamper resistant cover 101 from the tamper-resistant body 110, as well as additional motors 234a and 234b which may control gears 510 and external gears 332. For example, the controller may be a computing device which is capable of encoding and decoding programmed instructions. The controller may contain a processor, memory, input and output devices. The controller may be a microcontroller. For example, the controller may be an ATmega328 microcontroller. The controller may control other components of the apparatus including the regulating unit 230, the limiting device 232, the locking mechanism 120, the dispensing unit 140 and motors 234a, 234b. The microcontroller may be integrated into a complex circuit board with all of the components necessary to run the display 103, connect serially with an external computer, and read threshold values from sensors inside the device. The microcontroller may also tell the device when to activate the dispensing mechanism, rotate the gates in the exit path, and lock or unlock the lid. There may also be sufficient memory in the microcontroller to hold prescription and patient information. For example, in one embodiment, the memory may be loaded with dosing, scheduling and prescription information wherein if there is sudden power loss, patient information and dosing schedule will not be lost.

In one embodiment, a custom printed circuit board (PCB) 415 may be designed and manufactured for the apparatus. In this embodiment, the PCB may be cut into two pieces: one that will fit in the lid and hold the microcontroller and other hardware, and one that will hold the input (such as buttons) and associated circuitry. Ribbon cables may be used to connect the PCBs to the other peripherals (i.e. motors, sensors, buttons, display screen, and USB adapter)

In some embodiments, the electronic components and peripherals may be located in the tamper resistant cover 101, including one or more PCBs, the display screen, the communication component, controller, and the locking motor. The remaining components may be located in the tamper resistant body 110 including the wheel motor, the upper dispensing unit motor, sensors, and the power source. The ability to completely detach the lid from the base may make it easier for the pharmacist to fill the prescriptions, for this reason, ribbon cable may be used to connect the microcontroller to the peripherals in the base may have a connector in the access compartment that can be disconnected when the lid is removed and reconnected when it is put back on.

The apparatus 100, including interior components, may be capable of being sterilized one or more times. In some embodiments, the apparatus may be configured such that components including any electronics, peripherals, PCBs, display screen, communication components, controllers, motors, sensors, wheels, gears, access compartments, interior surfaces and power sources, may withstand repeated sterilization techniques. By way of example, such sterilization techniques may include various forms of steam, heat, chemical, irradiation based sterilization such as ultraviolet radiation and any other sterilization form known or prescribed by the US center for disease control (CDC), FDA and EPA. In some embodiments, heat sterilization may include steam, hot air treatments or ozone emitting devices. Embodiments utilizing steam sterilization may include a processing time between 3-30 minutes. In other embodiments, sterilization may involve using ethylene oxide gas. The sterilization time with ethylene oxide gas may include 1-6 hours of processing plus 8-12 hours of aeration time.

Additional sterilization techniques which may be utilized and withstood by the apparatus 100 may also include by way of example one or more of the following sterilants: hot water, hydrogen peroxide, hydrogen peroxide gas plasma, gluraldehyde-based formulations, ortho-phthaladehyde, paracetic acid, hydrogen peroxide and paracetic acid mixtures such as oxonia, low temperature steam formaldehyde, wet pasteurization with a detergent cleaning, hypochlorite, ethyl alcohol, isopropyl alcohol, sodium hypochlorite, phenolic germicidal detergent, iodophor germicidal detergent, and ammonia or ammonium based germicidal detergent. The at least one sterilant used may be in the form of a sterilizing fog or vapor fog, atomized spray, directed spray or rinse. In other embodiments, the sterilant may be applied using a sterilant bath. The sterilant may be applied at an elevated temperature between 100-250° F. The sterilant may be applied for a period for a short period of time such as between 1-30 seconds, or the sterilant may be used to thoroughly soak the apparatus 100 for minutes or even hours and the amount of time needed to sterilize the apparatus may depend on the sterilant used and the activation of the sterilant. Sterilization may be followed by a drying period. In some embodiments, the drying period may include introducing sterile heated air. The air may be heated to 230° F. In one embodiment, sterilization may occur by heating the tamper resistant body 110 to approximately 131° F. In some embodiments a sterilant such as hydrogen peroxide may be heated between 100-120° F. and the sterilant may be applied for approximately one second followed by 24 seconds of applying hot sterile air.

Alternative embodiments may withstand irradiation methods for sterilizing the components of the apparatus 100 including ultraviolet germicidal radiation, exposure to UV led lights, UV-C light, a pulsatile UV lamp such as the Steripulse-XL®, gamma radiation from for example a Cobalt 60, particulate radiation from accelerated electrons, or radiation from other radiation emitting devices.

In an alternative embodiment, the components of the apparatus 100 may be configured to withstand such sterilization by encasement within the same or substantially similar tamper-proof material of which the exterior of the apparatus 100 or the encasement may be made or any material that is capable of withstanding the desired sterilization technique selected. For example, if a the hydrogen peroxide, paracetic acid or a combination thereof is used to sterilize the components of the apparatus, components which may be damaged if they come in contact with the sterilization fluid may be encased in materials known to withstand the hydrogen peroxide or paracetic acid such as high density polyethylene (HDPE) or polyethylene terephthalate (PET).

In another embodiment, sensitive components such as PCBs, microcontrollers, power sources and motors may be placed in compartments, made separate and distinct from any compartments containing or contacting the stored contents of the apparatus. The sensitive components may be shielded from the harsh sterilization procedures by a barrier made of any material capable of withstanding the sterilization procedures including any of the tamper-proof materials described herein.

In alternative embodiments, the apparatus 100 may be configured such that sensitive components, including any electronics, peripherals, PCBs, display screen, communication components, controller, locking motor, sensors, and power source are located in a centralized portion of the apparatus 100 which may be away from surfaces which may come in contact with the contents stored inside the apparatus. For example, sensitive components may be configured to be held within the apparatus cover 101, whereas the stored contents may only come in contact with non-sensitive components configured in the apparatus body 110. In this alternative embodiments, the apparatus 100 may have the cover 101 removed which contains all of the sensitive components while the body 110 and the non-sensitive components are sterilized.

In yet another alternative embodiment, components which may come in contact with the stored contents of the apparatus at any time during storage, retrieval or dispensation may be pre-sterilized and disposable. In this embodiment, an authorized used may remove the old, contaminated components such as the funnel of the access compartment 130, the limiting device 232, pathway 236, dispensing unit 140 and the exit orifice 107. In another alternative embodiment, the contents of the apparatus body 110 may be disposable. For example, pre-manufactured, pre-sterilized apparatus bodies containing all pre-sterilized parts may be simply swapped by the authorized user prior to filling the apparatus with the contents.

In some embodiments, a software program may be uploaded to the controller. The microcontroller may control the motors, sensors, buttons, and display and may further be used to program the apparatus to dispense the contents according to the input of an administrative user. An Arduino Integrated Development Environment (IDE) may be used to write the software and download it onto the microcontroller. Arduino's sister project, Processing, is the open source program that may also be used to design an interface that allows an administrative user to program the device. The interface may be upgraded to be compatible with current pharmacy software and to be more secure.

To program the apparatus 100, it can be connected wirelessly to a computing device, or via communication cables using a communication port of the apparatus. For example, a USB cable with a Type A connector on one end and a Type B connector on the other may connect the apparatus to the computing device. In other embodiments an Arduino Mini USB Adapter may be used to provide the serial communication from the computer to the microcontroller. The USB adapter may convert information from the interface on the computer to 5 volt transmit and receive signals that are recognized by microcontrollers such as the ATmega328. Communications may be encrypted.

In one embodiment, the controller may be placed in communication with user interface 105 and the display device 103. A user or an individual authorized to access the apparatus 100 may do so by providing a specified input into the user interface 105 or by using a combination of inputs which the controller may be programmed to recognize. Upon recognition of a security input, the locking mechanism may respond accordingly. For example, in one embodiment, in response to a valid input, a controller may disengage a locking mechanism 120 which may allow for the separation of the apparatus cover 101 from the apparatus body 110 exposing the access compartment 130. In another embodiment, a controller may be programmed to lock the apparatus at the direction of the user. For example, upon inputting a preprogrammed valid security input via the user interface, the controller may engage the locking mechanism 120 such that the apparatus cover 101 and the apparatus body 110 may not be separated without extreme excess force or without reentering the security input.

In one embodiment, the interface may be password protected to ensure that only an authorized person programs the device. Once the correct security input is entered, the pharmacist or other administrative user can unlock and lock the device via the user interface 105. Important information, such as information regarding the pharmacy, the patient and the prescription, may be entered in the respective text fields on the interface which may then be transferred to the microcontroller. When the microcontroller receives the information, it may display it on the display screen so that the pharmacist can verify that it was stored correctly. That information may then be written in non-volatile memory so that even if the device loses power, the information will not be lost. In an embodiment using ATmega328 microcontroller, EEPROM (Electrically Erasable Programmable Read-Only Memory) which is limited in the number of times it can be successfully reprogrammed to 100,000 write/erase cycles may be used. Subsequently, the patient may then enter a pin, password or other input on the device. This input may be entered or requested whenever it is time to dispense a pill or pills.

The locking mechanism 120 may be an electronic lock which may include locking hardware or locking arms 440 controlled by a motor 215. In one embodiment, the motor may be connected to a microcontroller. In this embodiment, the microcontroller may send a signal to the motor based on user input such as a correct passcode, information provided by an administrative user from a networked external computing device via the communication or any other means for communicating that an administrative user may access the interior of the apparatus. To unlock the lid, once the signal to unlock is sent to the microcontroller, the microcontroller may initiate the motor 215 and the motor may rotate counter-clockwise causing the arms or locking hardware to retract from the locking ends 301 and 303. To lock the lid, a signal or user input may be sent to the microcontroller instructing it to lock the apparatus. Upon receipt of the locking input, the microcontroller may initiate the motor 215 clockwise, rotating the motor 215 clockwise and extending the locking hardware 440 locking end 303, biasing the locking hardware against the apparatus preventing removal of the cover 101.

In an alternative embodiment, the locking mechanism 120 may consist of a quarter turn snap feature that orients and fastens the lid in place. When turned, locking hardware 440 such as locking pins may extend to secure the snapped locations. The locking pins may be connected to a rotating center disk 442 so that the pins are forced outward as the disk 442 rotates. The rotation of the disk may be controlled electronically to prevent physical tampering of the locking mechanism. In yet another embodiment, the locking mechanism may consist of a motor, a rotating disk 442, four pins 440, a motor housing, a pin housing body with extended nubs, and a lock ring 303. The lock ring may be inserted into the top of the shell of the device and oriented into place on the four support ribs. The ring is may be glued down with an epoxy, or fastened through other operable means. The four pins may be fastened to the rotating disk 442. Then the rotating disk 442 may be also fastened to the motor. These components may be loaded into the pin housing body which may have four nubs or extensions at 90 degree angles from each other that are inserted into the lock ring and turned a quarter turn until they snap into a secure place. In order to secure the lid, the motor may rotate causing the locking arms to extend under the lock ring into the base of the device, securing it in place. To unlock the lid, the motor may rotate in the opposite direction causing the locking arms to retract into the lid.

In yet another alternative embodiment, a controller may respond to a correct preprogrammed input by displaying confidential or restricted information on the display 103. In yet another alternative embodiment, the controller may be programmed to respond to an improper input by a user. For example, a locking mechanism may be programmed to report attempts to improperly access the apparatus 100 to an authorized individual such as the prescribing doctor, prescribing dentist, physical therapist, nurse, or pharmacist. Communications may be sent by the communication component (wirelessly or via cable communications) and may be directed by the controller, to an external computing device or alert an authorized individual.

In some embodiments, the locking mechanism 120 may only function after the lid is connected to a computer or other external computing device, for example using a USB cord and the administrative user has entered a password. With the lid unlocked medication may be loaded into the device. Once loaded and programmed the lid may be snapped back on and locked by the administrative user such as a pharmacist. The loaded device will then be in the possession of the end user and the lid cannot be removed without excessive force, thus damaging the device in a noticeable way.

The controller may control the regulation of drug delivery by the tamper-resistant drug-delivery regulation apparatus 100. In one embodiment, the controller may be programmed with a governing protocol which may control drug and content delivery, wherein the governing protocol may be operable with linked data-memory. The memory may store information about the patient, contents of the apparatus and special instructions. The memory may include the type of drug contained within the device, how the drug is to be administered, important medical history pertaining to the intended recipient, patient-specific notes and instructions from administrative users, including pharmacists and/or prescribing doctors, and a log of the frequency of drug delivery via the device, dosing schedule, dosing amount, access codes, inputs for circumventing security features and/or any other like information that can facilitate legal and proper patient medication in accordance with prescriptions by authorized medical personnel. The governing protocol may be programmed and altered by an external computing device and may send and receive stored information using the onboard communication component.

In the exemplary embodiment, the microcontroller may contain the governing protocol of the device. The governing protocol may control drug delivery according to dosage and time of delivery as set in the programming by an administrative user. In one embodiment, the microcontroller may include a timer to track when the next dose will be administered. In one embodiment, the apparatus may be capable of using a timer. In some embodiments, the timer may include a wait time between one second and 52 days between administered doses. When the timer expires, the user may be prompted on the output device 103 or an audio output to retrieve their next dose. For example, a user may be prompted to enter a password or other user input when the timer expires, upon entering the designated user input, the dose may be dispensed. In an alternative embodiment, the governing protocol, may be coupled to operable device memory.

In one embodiment, the timer may control how often a dosage is dispensed. Each time the timer expires, the display may output a message or a sound to indicate that it is time for another dose. The program may then wait for the user to enter the correct input. When the correct input is entered, the dispensing process begins. After a dosage has been dispensed, the timer may be reset which keeps track of how long until the next dosage will be available. The program may also keep track of how many pills are left in the apparatus. For example, in some embodiments, after it dispenses the last pill, the display may present a message that indicates there are no remaining pills. In other embodiments, a user may verify the number of remaining doses by entering an input programmed to display how many pills are left and how much time is left until the next pill. In alternative embodiments, in order to conserve battery life, whenever the device is not dispensing a dosage or responding to a button pressed by the user, the microcontroller may be put in power-save mode. When in this mode, the timer still continues to run, allowing the schedule to be kept, and interrupts still work, meaning that the microcontroller will "wake up" when input is entered or when the timer goes off.

In some embodiments, the operable device memory may be linked to external data sources either wirelessly or via wired communications, such as Wi-Fi, Bluetooth, Ethernet cables, powerline network adapters, RFID and any other means of network communication using the onboard communication component. For example, information may be networked between the apparatus's controller and a database or file containing all the programmed information which may be stored in a separate location such as a server, or separate computing device.

Figure 3:
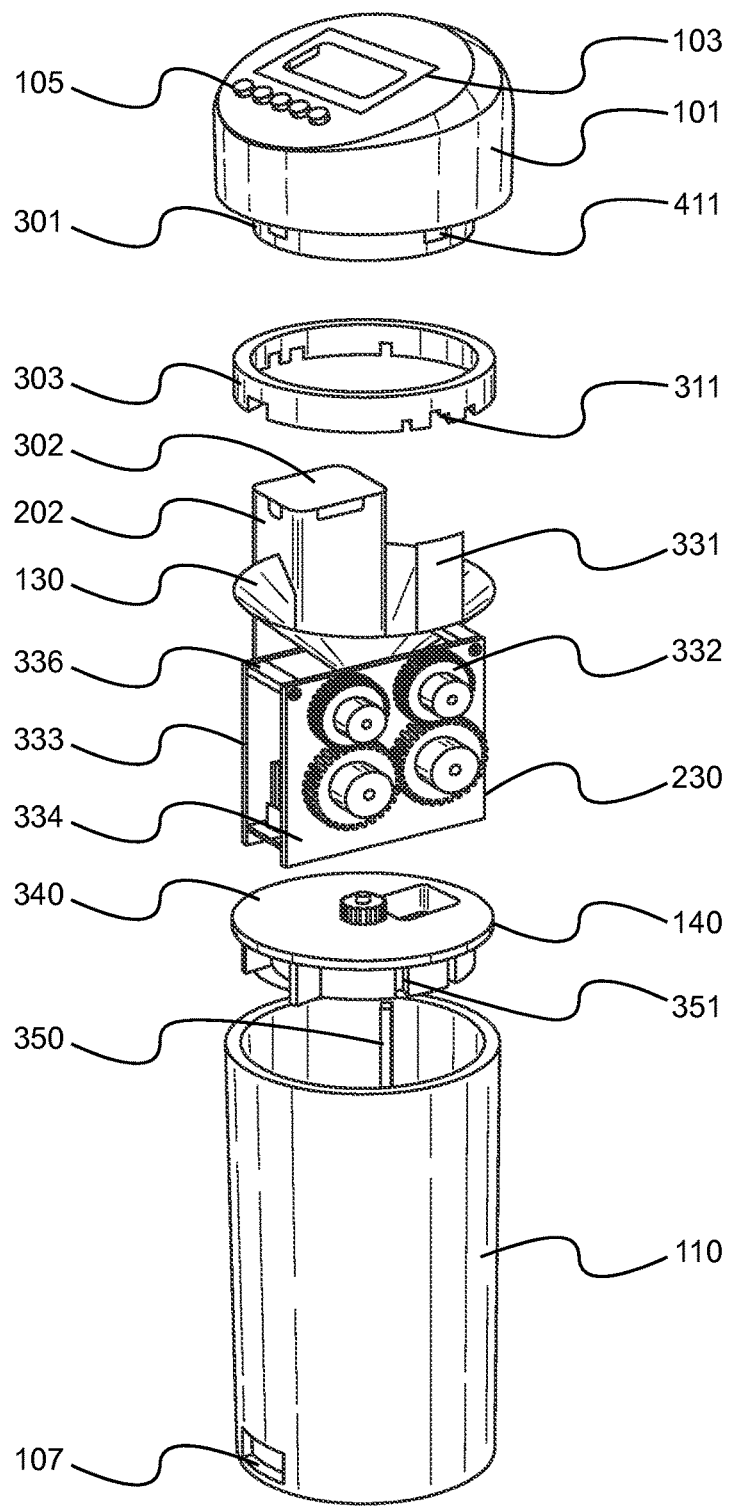
FIG. 3 depicts an exploded view of the embodiment of an apparatus for receiving, dispensing, and regulating a controlled substance depicted in FIG. 1.
Figure 4A:
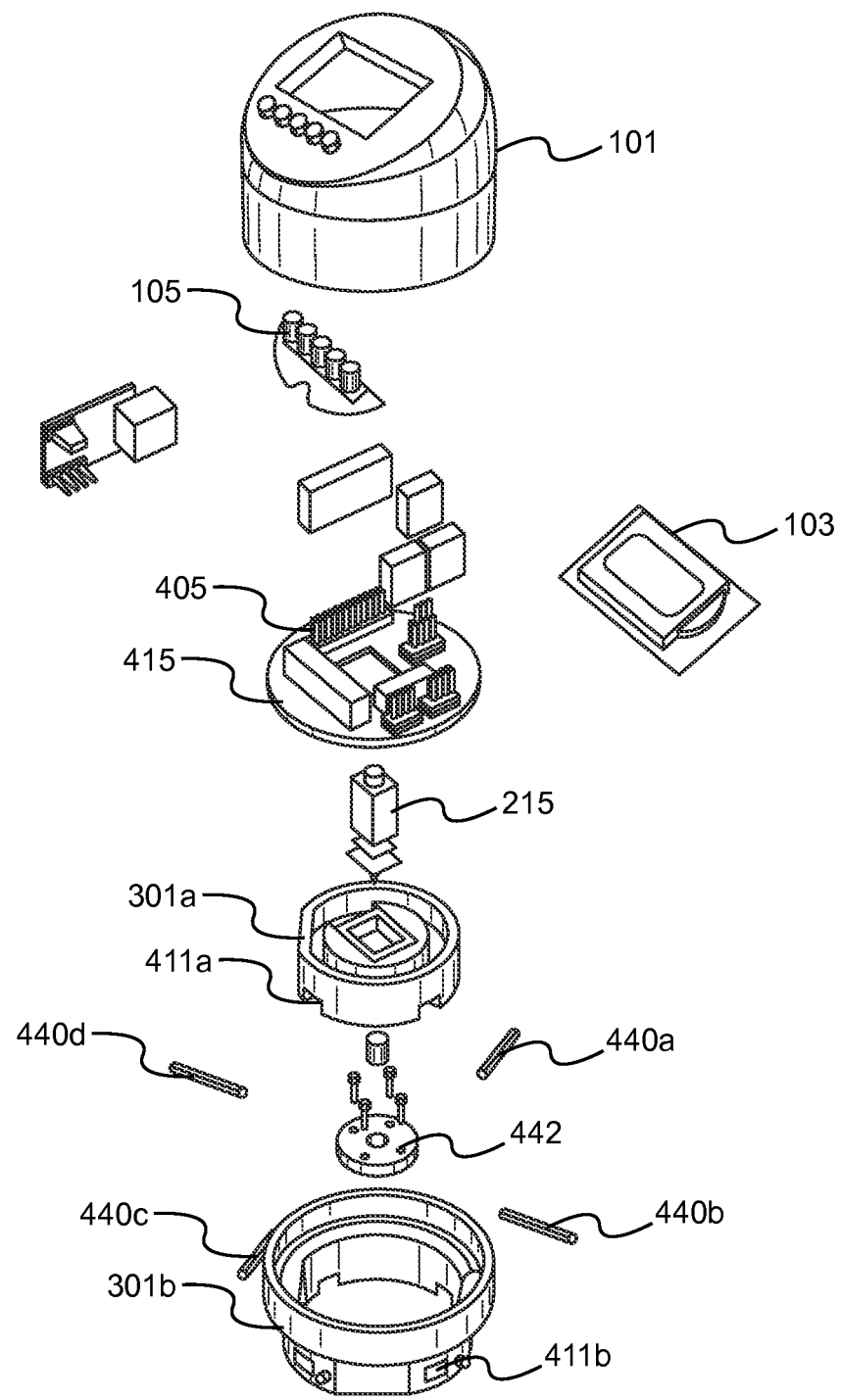
FIG. 4A depicts an exploded view of an embodiment of a apparatus cover of an apparatus for receiving, dispensing, and regulating a controlled substance.
Figure 4B:
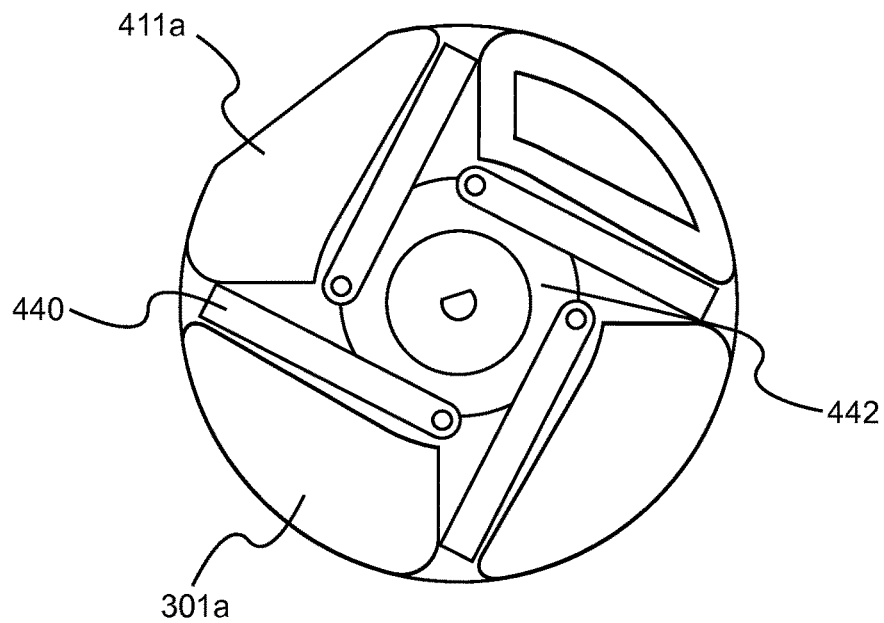
FIG. 4B depicts a bottom view of the interior portion of a first locking end of a locking mechanism in an unlocked position.
Figure 4C:
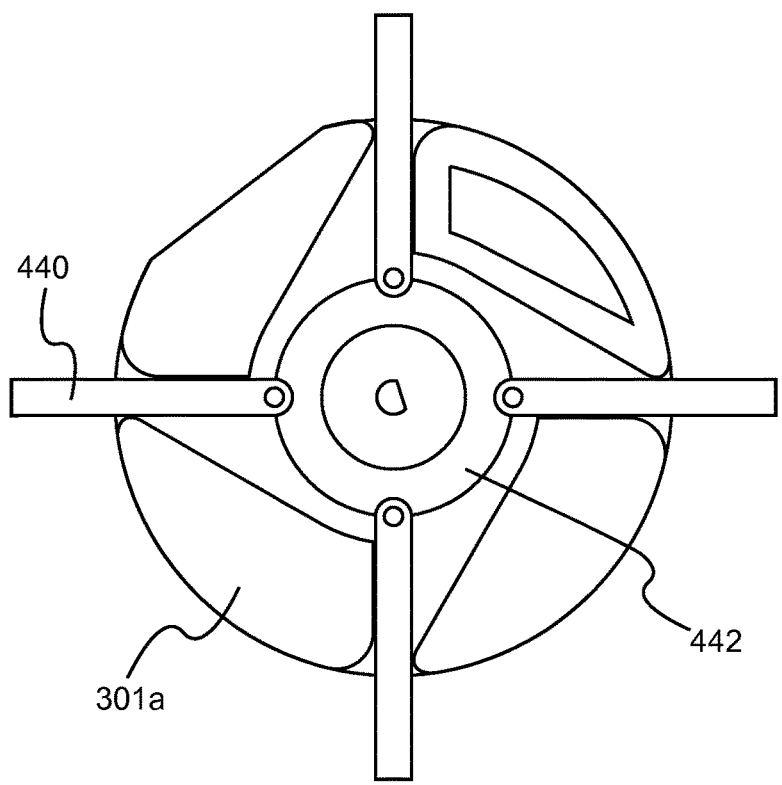
FIG. 4C depicts a bottom view of the interior portion of a first locking end of a locking mechanism in the locked position.

Referring to FIGS. 2, 3, and 4C, the controller may control a locking mechanism 120. The locking mechanism may be any sort of device or contraption which prevents unauthorized entry. For instance, the separation of two portions of the apparatus may be prevented, unless authorized. In the exemplary embodiment, the two portions that are separated are the apparatus cover 101 and the apparatus body 110. The apparatus is not limited to this single configuration and may include any number of segments in any number of positions of the apparatus 100. The locking mechanism 120 may be the device which holds the two or more segments of the apparatus 100 in place when the apparatus segments are connected. The apparatus may include multiple locking mechanisms 120. For example an apparatus may include three segmented pieces including a top, middle and bottom. A first locking mechanism may exist at the interface between the top portion and the middle portion, while a second locking mechanism may exist at the interface between the middle portion and the bottom portion.

The locking mechanism 120 may itself be constructed of multiple components. In one embodiment, the locking mechanism may include a first locking end 301 and a second locking end 303. In the exemplary embodiment, the first locking end 301 may interlock or nestle within the second locking end 303. In the exemplary embodiment, the first locking end 301 fits within the second locking end 303, however, in alternative embodiments, the second locking end 303 may nestle within an overlapping first locking end

301. The first and second locking ends may be any shape or size. As shown in the referenced figures, the first and second locking ends are circular in shape, but such a designated shape is not limited to circular and in fact the locking mechanism embodiments may be any operable geometric shape.

The locking mechanism's 120 first and second locking ends 301, 303 may include a plurality of bores or slots 311, 411. The plurality of bores or slots 311, 411 may line up when the first and second locking ends 301, 303 are nestled within each other. In one embodiment, at least one piece of locking hardware 440 may be extended through the bore or slot 311, 411. When a piece of locking hardware, such as a locking arm 440 extends through the first and second locking ends 301, 303 the mechanism may be said to have been placed in the locked position. In another embodiment, the locking hardware may reside within the interior locking end when the first and second locking ends are nestled within one another. The locking hardware may extend outward from the first locking end's 301 bore 411 and protrude into the second bore or slot 311. The locking hardware 440 extending through the locking ends 301 and 303 bores or slots 311, 411 may prevent the separation of the apparatus 100 segments. Likewise, if the at least one fastener 440 does not extend through the bores 311, 411 of both first and second locking end 301, 303 the segments of the apparatus 100 may be separated. The locking hardware 440 does not need to protrude or intrude between the first and second locking ends in order to lock or release the apparatus segments. In an alternative embodiment, the first and second locking ends 301, 303 may contain a magnetic ends which attract to each other when placed in a locked position and repel each other when placed in a released mode, thereby allowing the first and second ends 301, 303 to separate.

In yet another alternative embodiment, the first locking end 301 may include an interior portion 301a and an exterior portion 301b. This embodiment may be advantageous because the locking mechanism may be unseen by the user. In this alternative embodiment, the interior portion and exterior portion 301a, 301b may fit inside one another. Each portion 301a, 301b may include bores or slots 411. These bores or slots 411 may line up with one another for allowing locking hardware to extend and retract accordingly. The interior portion 301a may also contain bore capable of receiving the locking hardware 440 such as a locking pin. In an alternative embodiment, the locking control mechanism may directly adjust and control the position of the internal portion 301a of the first locking end 301 instead of the locking hardware itself. For example, the locking control mechanism may exert an action on the internal portion 301a such as a twisting motion or rotating motion. This motion on the internal portion 301a may affect the extension of the locking hardware 440 in relation to the external portion 301b thus ultimately affecting whether or not the locking hardware 440 extends through interface between the first and second locking end 301, 303 or not. The rotation of the internal portion 301a may be controlled electronically by the controller and the rotation of the internal portion may force the locking hardware outward as the disk rotates.

In yet another alternative embodiment, the rotating disc 442 may be replaced with a center gear and a series of gears attached to each piece of locking hardware. Upon receiving the signal to lock or unlock, the controller can initiate a motor attached to the center gear and begin rotating the gear accordingly, thus rotating the gears attached to the locking hardware.

Embodiments of a locking mechanism may also include a mechanical lock, an electronic lock, an electrical lock, and electromechanical lock, a sonic lock, an optical lock or any operable combination thereof. Locking mechanisms may include keyed locks, combination locks, fingerprint identification locks, RFID locks, security token locks, password protected locks, or any means of securing an opening from unauthorized access. The passwords, security tokens or other opening means may be correlated with a unique ID assigned to the apparatus 110, wherein the unique ID may also be correlated to a particular user being authorized to access the contents of the apparatus 100. Embodiments of locking mechanisms may be unlocked directly or remotely. Embodiments of directly operated locking mechanisms may include locking mechanisms which are unlocked from a location which is the same as the location of the apparatus. Embodiments of remotely operated locking mechanisms may include locking mechanisms which are unlocked from a location which is different from the location of the apparatus. Those skilled in the art should appreciate that there may be other embodiments of a locking mechanism. The locking mechanism may utilize electrical power, such as an electric motor, may be magnetically functional, may be mechanically operable, or any like combination.

In one embodiment, the controller may be placed in communication with the at least one piece of locking hardware 440. The controller may control the extension and retraction functions of the at least one piece of locking hardware 440. In one embodiment, the locking mechanism 120 may engage or disengage the at least one piece of locking hardware in response to programmed instructions. For example, in one embodiment, the locking mechanism may be programmed to release or engage the at least one piece of locking hardware 440 after a predetermined amount of time. At such intervals, the tamper-resistant drug-delivery regulation apparatus 100 may allow for the removal of one tablet or one prescribed dose of controlled substance, wherein a prescribed dose may include more than one tablet, vaporized spray, liquid volume dispersion, or other dosage release. After a prescribed dose is removed the apparatus' governing protocol, such as a timer, may automatically reset, or otherwise control operability of the apparatus, and may not allow additional contents to be dispensed until the next programmed dosage interval. The apparatus' timer may reset to the proper interval upon the manipulation required to remove a dose so that additional pills, tablets or capsules may not be obtained if a scheduled dose is missed. By this means the intended recipient is prevented from inadvertently or purposefully obtaining excessive controlled substances within an unduly short period of time. Those in the art should appreciate that other timing mechanisms and time-regulatory devices may be utilized to control dispensing.

In another embodiment, the locking mechanism 120 may disengage or reengage at certain times of the day or on specific days. For example, if a prescription calls for a pill every two to four hours, the pills may be accessible from the tamper-resistant drug-delivery regulation apparatus 100 every two hours. If a period of time passes which exceeds the four hour time frame, such as at night, a pill may be available since the two hour minimum time has passed. A log stored in the device memory may also be accessed by administrative users or those having appropriate permission (such as doctors, pharmacists) through authorized communications or user interface actions with the device (wirelessly or through wires) to evaluate whether the previously stored medication was, in fact, dispensed from the device in accordance with the manner prescribed. In some embodiments, if the log reveals anomalies in drug dispersion intervals and dosages, the authorized personnel can be made aware and can take action, as deemed necessary. For example, the administrative user may decide to permanently lock the apparatus until he meets with the patient to discuss the logged anomalies.

The tamper-resistant drug-delivery regulation apparatus 100 may be provided with a unique device identification number or a user ID number which can be correlated to specific users. Hence, authorized personnel may be able to determine the unique identity of the device and match the device to the specifically correlated user to make sure the proper user is associated with the device. Such an identification-based correlation can act as a check against possible mistakes by pharmacists in accidentally switching similar-looking devices or prevent non-administrative users from falsely associating themselves with a device in hopes of obtaining drugs.

In another alternative, the locking mechanism may be programmed to disengage when the access compartment or reservoir 130 is empty. In yet another alternative embodiment, the locking mechanism 120 may be disengaged or reengaged when there is an acceptable input on the user interface or a networked external computing device communicating with the apparatus via the apparatus's communication component. For example, an authorized individual charged with refilling the access compartment 130 may disengage the first and second locking ends 301, 303 by inputting an access code, thumbprint scanning, retinal scanning, face scanning, bar-code scanning, swiping a key card, inserting a key or coded key and combinations thereof. The prescribed input may send a signal to the locking mechanism, wherein the controller may facilitate engagement or disengagement of the locking mechanism 120 accordingly.

An access compartment 130 may be refilled by an authorized individual such as a physician or pharmacist. The compartment may be refilled by simply pouring or manually placing each prescribed dose into the access compartment. In an alternative embodiment, a quick loading container or preloaded container which contains all of the doses prescribed may be placed in the access compartment.

Embodiments of the tamper-resistant apparatus 100 may include at least one securable opening or access compartment 130 for receiving and dispensing a substance or controlled substance. The access compartment 130 may act as a reservoir or storage hopper for holding the contents of the apparatus 100 prior to distribution or administration of the contents to exit path 107. The access compartment 130 may be inaccessible by individual users of the apparatus and may be restricted by authorized personnel charged with maintaining the contents of the apparatus at an acceptable level. In one embodiment, the access compartment 130 may be located beneath the locking mechanism 120. In this embodiment, in order to achieve access to the access compartment 130, an administrative user may release the locking mechanism 120 and thus separate a first and second segment of the apparatus 100. In the exemplary embodiment, the access compartment lies beneath the locking mechanism within the apparatus body 110. The access compartment 130 may be accessed by releasing the locking mechanism 120 and then separating the apparatus cover 101 from the apparatus body 110, thus revealing the access compartment 130.

The access compartment 130 may include a reservoir for holding the contents that may be provided by authorized individuals for dispensation. Embodiments of an access compartment 130 may include a plurality of internal compartments. Embodiments of a plurality of internal compartments may include two, three, four, or any number of desired internal compartments. Furthermore, different internal compartments may be configured to accept different types of substances. For example, an access compartment may have three internal compartments. Of those three internal compartments, one may be configured to contain a solid controlled substance, as in a pill or tablet, one may be configured to contain a liquid controlled substance such as a solution or suspension and one compartment may be configured to hold a gaseous controlled substance such as an inhalant or aerosol. Moreover, embodiments may be configured wherein two compartments contains a solid controlled substance, and another compartment contains a liquid controlled substances. Each compartment, the associated regulating mechanism and dispensing unit may prevent unwanted access to the various controlled substances and may effectuate dispensing according to a prescribed schedule.

Embodiments of internal compartments may have an internal ramped surface for collecting and dispensing controlled substance. Embodiments of an internal ramped surface may include a conically shaped surface, a corkscrew shaped surface, or a ramped surface with a curve in it. Embodiments of a ramped surface with a curve may include a surface which curves 180 degrees, or nearly 180 degrees, or any other amount which would help to prevent an unadministrative user from accessing the compartment from the outside. Those skilled in the art should appreciate that there may be other embodiments of internal compartments.

In one embodiment, the access compartment may also include an area for encasing 202 a power source 322. In alternative embodiments, the power source may be located elsewhere within the apparatus such as within the apparatus cover 101. For example, an the alternative embodiment, the power source may located in the bottom portion of the cover 101. The power source may include a power source cap 302. The power source cap may be used to seal the power source off from any moisture or liquids that may be present in the access compartment. For example, a liquid dosage form may be placed in the access compartment. The power source cap 302 may prevent the liquid dosage form from entering the power source encasement 202. The power source may supply electrical energy to other components of the apparatus including the locking mechanism motor 215, display 103, user interface 105, a regulating device 230, regulator motors 234a, 234b and dispensing unit 140.

The power source compartment may easily accessible by the pharmacist or other administrative user when the lid is off. The power source may be rechargeable or the power source may be substituted with each prescription refill. There are several strategies to improving of the power source's lifespan. In one embodiment, the circuit may incorporate low-power components. Different microcontrollers may include different energy efficiencies. In another embodiment, a relay to control when the peripherals are connected to the pins of the microcontroller may be used. For example, if just a small-voltage signal is applied to the relay, it will act as a switch and connect the displays, input devices, motors, and sensors. When the signal is not applied to relay, those components will be independent and may not draw any power from the power source.

The power source 322 may be anything capable of supplying electrical power to an electrical load. Embodiments of a power supply may include rechargeable or non-rechargeable batteries such as nickel cadmium batteries or lithium-ion batteries, nine volt batteries, wall outlets, solar panels, AC, DC or AC/DC power supplies, linear power supplies, switched mode power supplies, AC adapters, uninterruptable power supply, solar, light-powered, fuel-cell powered, and combinations thereof. In an alternative embodiment, a two or more power supplies may be used. Multiple power sources may be capable of providing additional time which the apparatus may be used without recharging or the additional sources may be backups in case of power failure. For example, an apparatus may be supplied by a wall outlet and a battery backup. In the event that the apparatus 100 is not able to receive power from the wall, outlet, the battery backup may turn on, thus still allowing for the locking mechanism to be disengaged or the contents to be dispensed even in the event of a power failure. In an alternative embodiment, the apparatus may include a charging station or charging dock. The apparatus may nestle and connect with the charging station. Upon affixing within the station, the power supply may be re-energized. The microcontroller may be programmed to monitor charging status. In alternative embodiments, the microcontroller may restrict the flow of power to the power supply once charging is complete. This may prevent overcharging the power source, and thus ultimately lengthen the amount of energy that can be stored by the battery, thus increasing overall battery charge, for the life of the battery.

In some embodiments of the apparatus 100, the controller may be programmed to enter a power saving mode. For example, the controller may be set to wake up after a certain amount of time, or upon input by a patient or administrative user. In another embodiment, the controller may prevent power from being drawn by the components such as the display, input interface or the motors unless there was activity by a patient or administrative user.

There are several strategies to improving battery life. One option is to design the circuit to incorporate low-power components. For instance, with regard to the above-described embodiment, the ATmega328 could be switched for a different microcontroller which is made to control systems that are very energy efficient. Another option is to use a relay to control when the peripherals are connected to the pins of the microcontroller. If just a small-voltage signal is applied to the relay, it will act as a switch and connect the screen, buttons, motors, and sensors. When the signal is not applied to relay, those components will be independent and not draw any power from the battery. Other options also include using a rechargeable battery. Still further solutions may be implemented to extend the battery life of the device. Moreover, power regulation with respect to all components of the apparatus may be taken into account, such as considerations pertaining to a component like the USB adapter that may affect the power consumption when it is not in use.

One embodiment of the tamper-resistant apparatus may include a regulating device 230. The regulating device may be any instrument capable of limiting or controlling the amount of contents within the access compartment 130 from reaching the exit path 107. In the exemplary embodiment, the regulating device may be placed in direct contact with the reservoir of the access compartment 130 thus preventing the contents received within the access compartment 130 from improperly migrating to the exit path 107. The regulating device 230 may comprise a first regulator plate 333, a second regulator plate 334, a pathway 236, a limiting device 232 and a limiting device driving mechanism 332.

In one embodiment a dose regulating device 230 may be comprised of a first and second plate. In the exemplary embodiment, the first and second plate 333, 334 may be positioned parallel to one another. In alternative embodiments, the plates 333 and 334 may connect at an angle that is not parallel. The first and second plate 333, 334 may be fastened together using fastening hardware 338 such as screws, nails, staples, clips or any other hardware used fastening a structural piece to another structural piece. In an alternative embodiment, the first 333 and second plates 334 may be welded, epoxied, integrally molded or otherwise permanently affixed together, providing increased structural support for the regulating device 230.

The first and second plate 333, 334 may include a plurality of bores through their surface for receiving fastening hardware 338. In one embodiment one or more of the plates 333, 334 may include a bored spacer 336. The bored spacer 336 may connect to either plate and may provide a predetermined or expandable distance between the first and second plate. In addition, the bored spacer 336 may contain a path within its interior for receiving fastening hardware.

The dose regulating device 230 may include, in some embodiments, a pathway 236. The pathway 236 may be any structure or feature that helps to guide the contents stored in the access compartment to the dispensing unit 140. The pathway 236 may be shaped in such a manner that prohibits unauthorized access to the access compartment 130 from the exit path 107. The pathway 236 may be any shape, size or length. The pathway may contain raised edges which prevent the contents of the access compartment from spilling into other portions of the apparatus 100. In one embodiment the pathway 236 may contain angled sides or a funnel shape. In another embodiment, the pathway may be a serpentine shape while in an alternative embodiment, the pathway may a straight 90 degree shape or may include one or more ramped surfaces. One embodiment of the pathway 236 may include an elevator which may raise and lower along the pathway between the pathway 236 and the pathway receiver 736. The dispensed contents upon reaching the raised elevator may cause the elevator to lower. Once lowered the contents may enter the pathway receiver 736 of the dispensing unit 140. In an alternative embodiment, the elevator may be electronically raised and lowered. The elevator may include a sensor which communicates with the controller. Upon transmitting a signal to the controller, that the contents of the access compartment have been received, the controller may communicate to a motor 234a or 234b to raise or lower the elevator.

The pathway 236 may be welded, glued, screwed, or otherwise affixed to one or both of the plates 333, 334. In an alternative embodiment, the pathway may be a direct extension of the limiting device 232. In yet another alternative embodiment, the pathway 236 may be separate from the regulator device 230. The pathway may extend between the bottom of the regulator device 230 and the top of the dispensing unit 140. In an alternative embodiment, a pathway 236 may not be used. In this alternative embodiment, the contents of the access compartment 130 may be dispensed directly into the dispensing unit 140.

A regulating device 230 may include a limiting device 232 which may prevent or allow a controlled migration of the contents of the access compartment 130. There may be more than one limiting device 232. For example, in one embodiment there may be a limiting device operatively connected to each access compartment 130. In an alternative example, there may be multiple access compartments which may all lead to a common limiting device 232.

In one embodiment, the limiting device 232 may be controlled by the controller. The controller may engage or disengage the regulating device 230 to distribute the contents of the access compartment 130. The controller may distribute the contents based upon the receipt of a preprogrammed signal. For example, the controller may instruct the regulating device to engage in dispensing a controlled dose of the apparatus's contents based on an internal clock setting. In another embodiment, a regulating device 230 may engage in releasing the contents of the access compartment 130 at a specific time of day. In an alternative embodiment, the regulating device 230 may distribute the contents at a specified rate such as every four hours. In another embodiment, the regulating device 230 may be sent a signal from the controller when the controller receives an input from a user. For example, a user may supply a specific input entitling them to have the contents of the apparatus 100 administered. In an alternative embodiment, the user commanded distribution of contents may be restricted to only a certain number of times within a specified period.

In yet another embodiment, the apparatus 100 may receive input from an administrative user such as a doctor or pharmacist which manually tells the controller to send an instruction to the regulating device 230 to administer the contents of the access compartment 130. The administrative user may submit their own inputs to the apparatus 100 and controller via a network or through the apparatus's communication component.

In one embodiment, the limiting device 232 may be powered by a power source 322 directly. In one embodiment, the limiting device 232 may be controlled by one or more motor 234a, 234b. The motors 234a and 234b may be placed in communication with the controller. For example, the controller may receive an input from a user or preprogrammed instruction to administer a portion of the contents of the access compartment 130. In response, the controller may send a signal to engage the motors 234a and 234b. The motor 234b may initiate the limiting device gears 332 attached to the limiting device 232 causing them to rotate and allow for the migration of the contents of the access compartment 130 accordingly. In another embodiment, motor 234a may control the rotation of gears 510 allowing for the dispensing unit 140 to rotate and align the interior portion 242 enabling the dispensing unit to receive the contents of the access compartment being distributed. The limiting device 232 may be any apparatus capable of restricting the migration of the contents stored in the access compartment 130 from reaching the dispensing unit 140 or the exit path 107.

Figure 5:
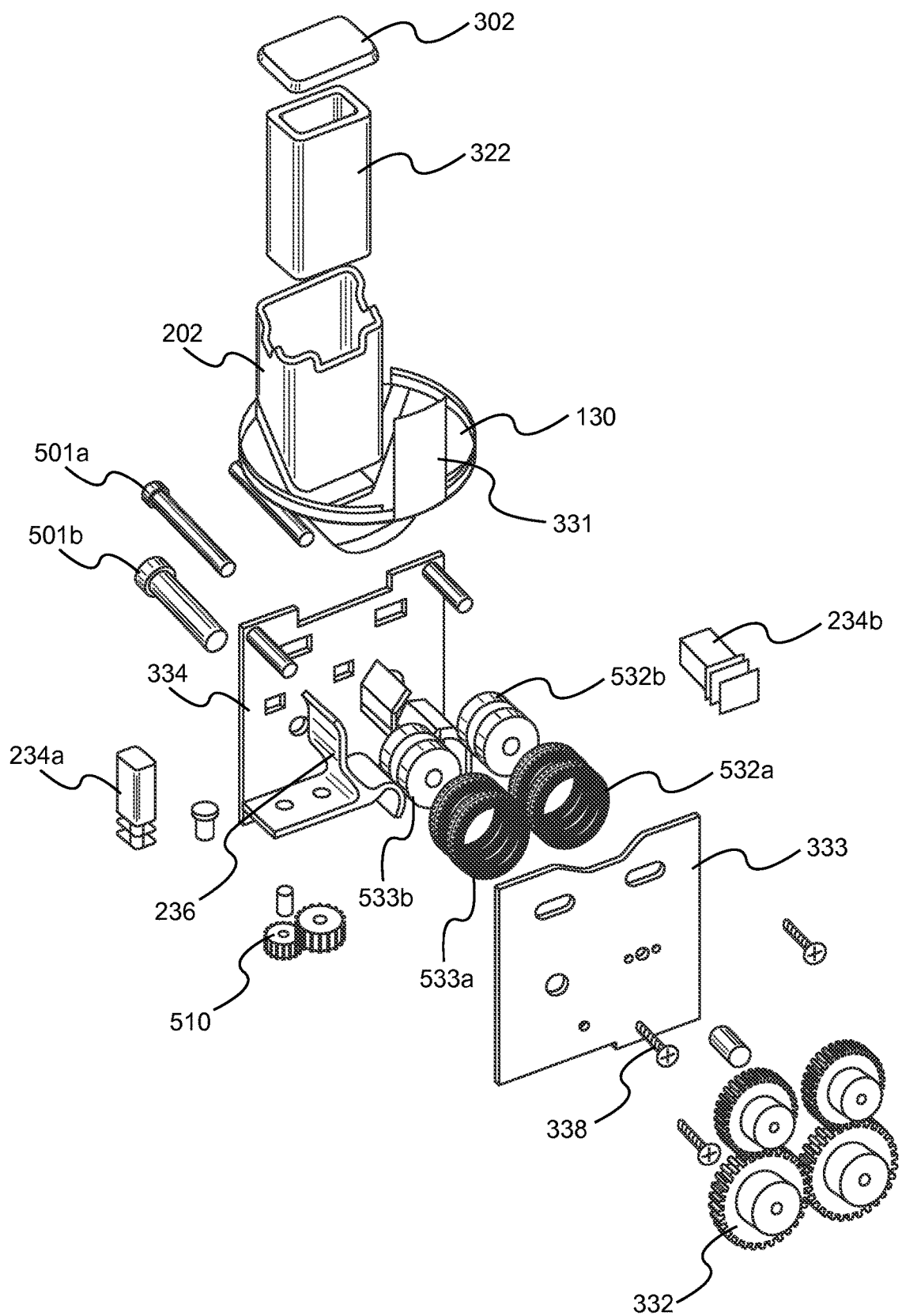
FIG. 5 depicts an exploded view of an embodiment of an access compartment and a regulating device of an apparatus for receiving, dispensing and regulating a controlled substance.
Figures 6A, 6B, 6C:
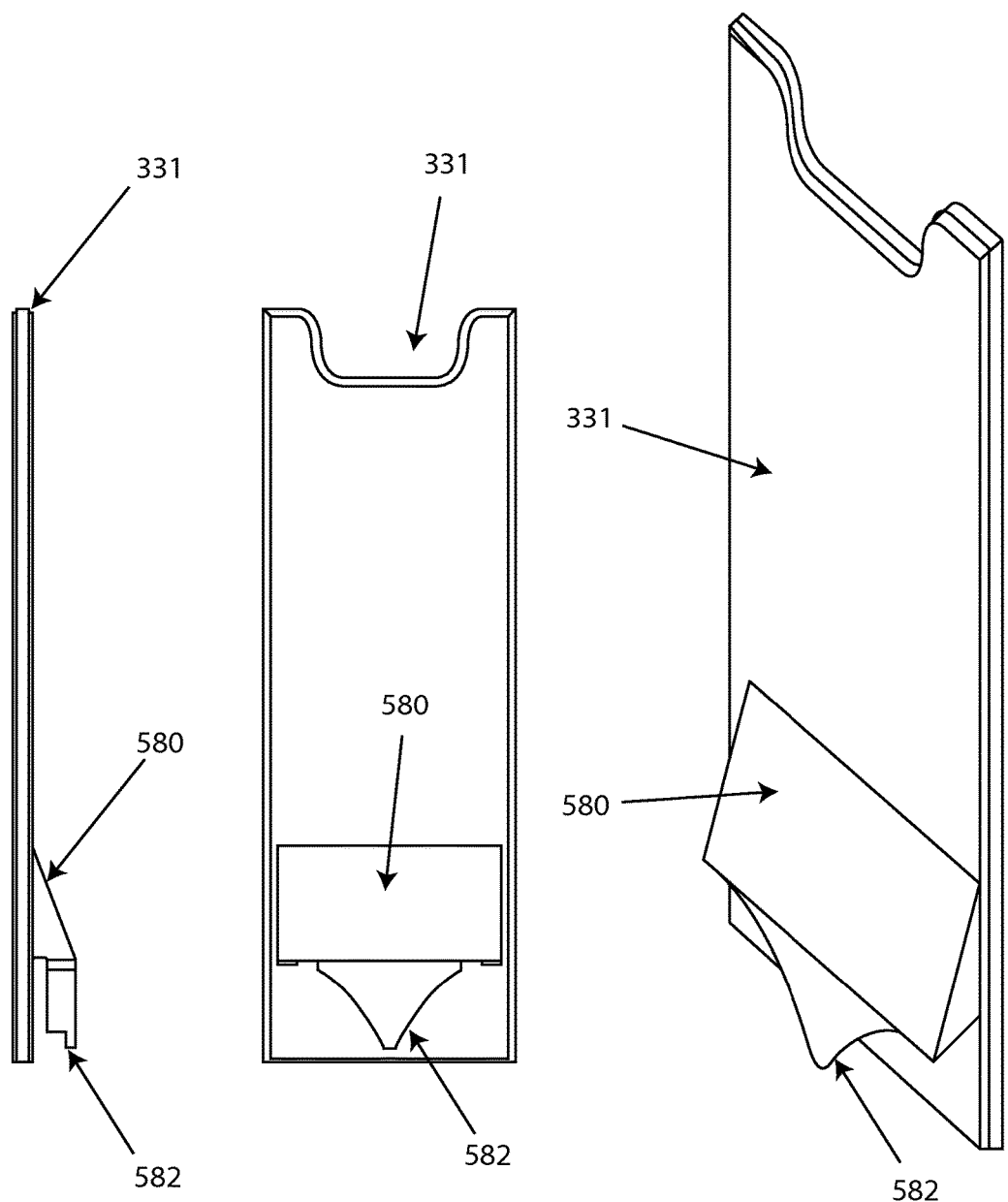
FIG. 6A depicts a side view of a variable insert.
FIG. 6B depicts a front view of a variable insert.
FIG. 6C depicts a perspective view of a variable insert.
Figure 7:
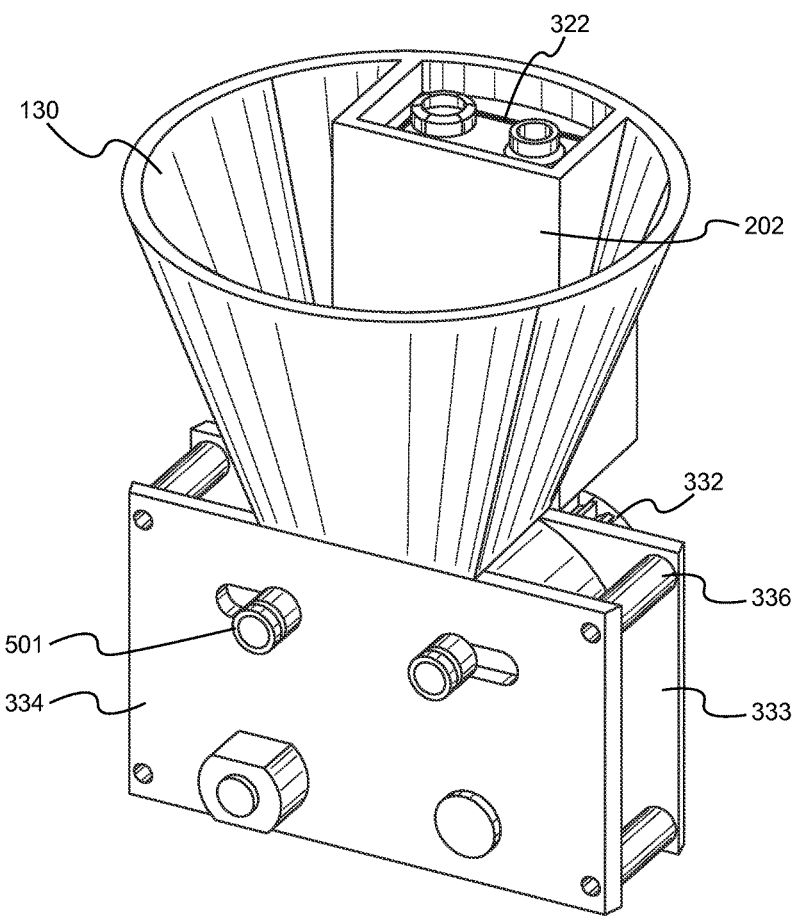
FIG. 7 depicts perspective view of the embodiment of the access compartment and dose regulator.

In one embodiment, the limiting device 232 may include a passageway that may be open or closed. The opening and closing of the passageway may depend on preprogrammed instructions determining when the passageway may open or in the alternative, an authorized input from the user interface or an external computing device networked to the apparatus 100. In an alternative embodiment the distributing device 232 may be a set of gears or wheels 532, 533. The wheels may be affixed to one or more plates 333, 334. For example, the gear shaft 501 may be threaded through one or more wall plates and through a bore in the gear 532. The gear shaft may be any piece of hardware which may extend through the gear and assert a rotational force allowing for the wheels 532, 533 to rotate. The wheels may be separated into a plurality of pieces. For example, as seen in FIG. 5, the wheels 532, 533 may include an treaded portion 532 A, 533A or geared teeth which may be placed over a rotational portion 532 B, 533B. The rotational portion may include sections or grooves for receiving the treaded portion and may further include a bore capable of receiving a gear shaft for rotating the rotational portion 533. In an alternative embodiment, there may be a plurality of external gears 332 placed in communication with the wheels 532, 533. For example, the shaft 501 may extend through wall plates into a set of lower external gears. Upon energizing the gear shaft to rotate, the lower external gears may rotate as well. Operatively attached to the lower external gears may be a set of upper external gears. The upper external gears may include an additional connector or gear shaft which may be threaded through the wheels 532, 533. When the lower external gears rotate, the upper external gears may rotate as well, ultimately rotating the internal gears 532, 533.

As shown in the figures, the wheels 532, 533 may include a friction based mechanism for preventing the flow or migration of contents to the exit path 107. In one embodiment, the limiting device 232 may be a pair of rubber or plastic wheels. The wheels 532, 533, when stationary may provide enough friction or pinch together in such a manner to restrict the flow of contents of the access compartment and prevent migration to the exit path 107. When the wheels are engaged or rotated, the contents of the access compartment may begin to migrate in a controlled fashion. In one embodiment, the wheels may provide for the migration of the contents of the access compartment by turning in the opposite direction of each other. For example, wheel 532 may turn clockwise while wheel 533 turns counter clockwise. The results of this opposing motion may feed the contents of the access compartment 130 into the pathway 236 and ultimately toward the exit path 107. In one embodiment, the amount of the contents may be controlled by using a motion sensor or volumetric sensor. For example as a pill or solid dosage form is released, it may cross a sensor. Upon triggering the sensor, the wheels or gears may reverse direction preventing any more of the contents from being administered. In an alternative embodiment, once a designated volume of liquid is dispensed into a volumetric measuring cup, the regulating device may cease allowing the contents of the access compartment from migrating.

In an alternative embodiment, at the bottom of the access compartment, the lower pills may rest on wheels 532, 533. The wheels may completely close the access compartment exit. To accomplish this they may be spring-loaded to stay shut. Once the dispensing signal is given the motor turns the system of gears, which may be set in parallel, rotating both wheels inward to the center. This inward rotation catches a pill and pulls it down out of the access compartment. The wheels may be forced apart by the pill, creating an exit opening. The springs may stretch to maintain a gripping pressure on the pill. The springs may be attached to each gear shaft, 501 or an axle, while still allowing the gear shaft or axle to rotate. The spring constant for these springs may be between 0.30 and 0.40 lbs/in. Once the pill is released from the wheels it falls down the exit path it may pass a reflective sensor. The sensor detects that a pill has been release and a signal is sent to reverse the motors. Reversing wheels then force the remaining pills back up into the hopper ensuring that only one pill was allowed to be dispensed.

In an alternative embodiment, the apparatus may try to dislodge jammed pills or other contents that are stuck near the wheels but may not be within range to be pulled through. The device tries to dispense for at least three seconds, at which point if it does not dispense the contents, the wheels may reverse direction and dislodge any pills then the apparatus may attempt to reengage and try to re-dispense the contents. Embodiments of the apparatus may loop through this cycle until a pill is dispensed.

Embodiments of apparatus 100 may include a dispensing unit 140. The dispensing unit 140 may be placed in communication with the regulating device 230. The dispensing unit may control the amount of the contents received from the regulating device 230 which may be fed into the exit path 107. Embodiments of the apparatus may include one dispensing mechanism 140 or a plurality of dispensing mechanisms. Embodiments of dispensing mechanisms may include one or a plurality of exit paths, doors, hatches, slides, ports, caps, covers, flaps, lids, closures, or other mechanism which only opens to dispense a controlled substance according to the prescribed dosage and schedule. Embodiments of a dispensing mechanism may have two doors separated by a lower dispensing unit or pill retrieval chamber 240. The dispensing mechanism 140 may be formed so as to not allow both doors to be open at the same time thus preventing tampering by liquid or other attempts at unscheduled, unauthorized removal of the controlled substance. Embodiments of a dispensing mechanism may be waterproof, moisture-tight, vapor-tight, UV-resistant, sonically-sealed or buffered, impervious to visible light, and/or resistant to other forms of electromagnetic radiation.

Figure 8:
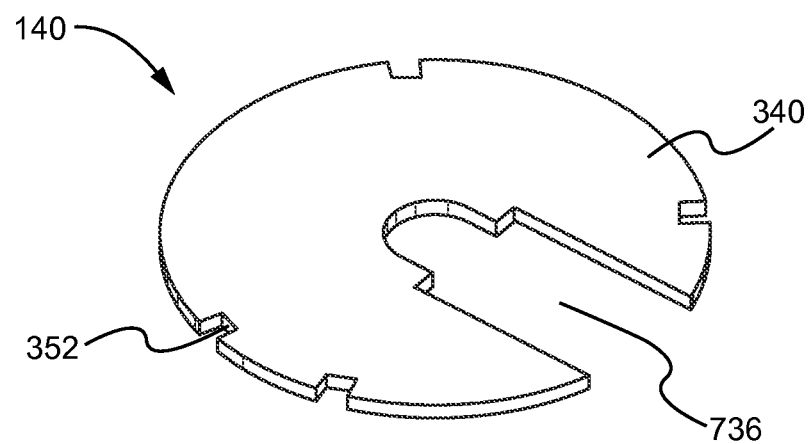
FIG. 8 depicts an exploded view of a dispensing device of an apparatus for receiving, dispensing, and regulating a controlled substance.
Figure 8:
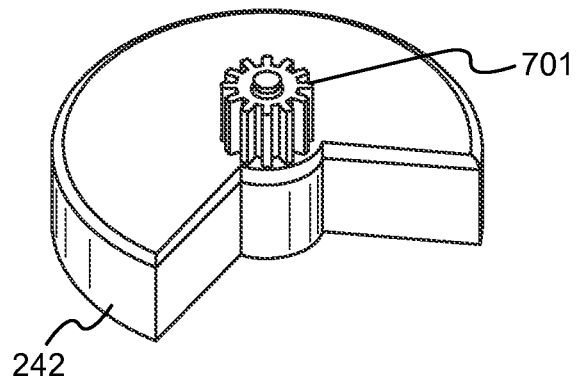
Figure 8:
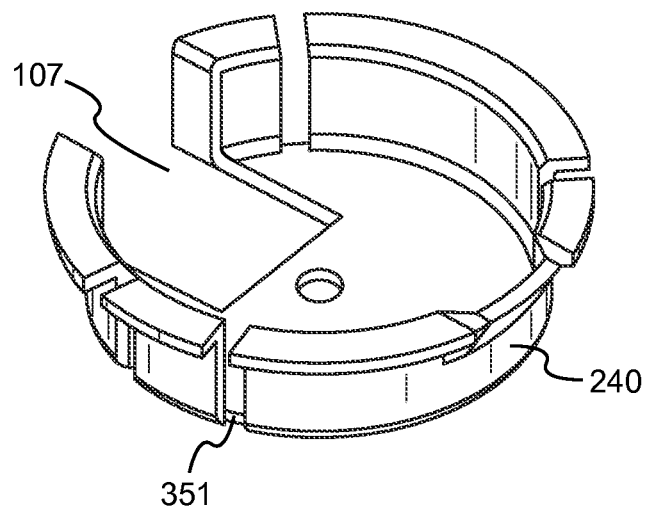

One embodiment of the dispensing unit 140 is depicted in FIG. 8. In this embodiment, the dispensing unit may include multiple pieces, including a cover 340, an interior portion 242 and a lower portion 240. The dispensing cover 340 may include a receiving path 736 which limits the entry of apparatus contents into the lower dispensing unit 240. In one embodiment, the receiving portion 736 may be placed in communication with the pathway 236. In another embodiment, the receiving portion 736 may be a slit, slot or notch cut into the dispensing unit cover 340. In another embodiment, the receiver 736 may be a sliding door, compartment or tray. In the exemplary embodiment, the receiving portion 736 may be 180 degrees opposite of the exit path 107 connected to the lower portion 240. This may allow for the interior dispensing unit 242 to operate in one half rotations wherein the first 180 degrees of the rotation aligns the receiving portion 736 with a gap or gate between the ends of the interior portion 242. The second 180 degree rotation may then pushes the contents loaded in the lower portion 240 into the exit path 107. While equidistant 180 rotations may be the exemplary embodiment, alternative embodiments may include any stroke rotation between receiving and dispensing the content of the dispensing unit 140.

In another embodiment, the exit path may start between the two support plates from the dispensing mechanism where the dose regulator path or channel guides the pill down to a resting point on top of the dispensing unit cover 340 or separator. The contents may wait for the interior portion or exit gate motor 234a to activate. The exit gate 242 may be a cylindrical piece with a wedge shaped section cutout. The motor drives the gears which then rotate the exit disc of the dispensing unit 140 until the cutout moves under the resting pill. The pill then falls into the cutout and is rotated 180° to the other side of the exit gate. As the pill passes the final exit of the device, it falls out and the user gains access to the pill. The exit gate 242 may then continue rotating to a random location or a preset location.

In another alternative embodiment, a dividing plate may be incorporated to separate the user from the contents of the access compartment. The dividing plate may act as extra security in the event that the interior portion or gate 242 is left in the aligned and open position with the exit path 107, a dividing plate may still act as an obstruction preventing such access.

In an another embodiment, the cover 340 may also include one or more slots or notches 352 which may be found along the perimeter of the cover 340. The slots 352 may interface with ridges 350 which may be located along the interior perimeter of the apparatus body. The ridge 350 and slot 352 interface may allow for dispensing unit 140 and other components of the apparatus to lock place and prevent shifting within the apparatus body 110 and may also act as a track for the components to slide vertically along when removing or replacing interior components.

The interior portion 242 of the dispensing unit 140 may work in conjunction with the cover 340 to restrict the flow of contents to the lower portion 240 and ultimately the exit path 107. In one embodiment the interior portion may include a section cut out that may align with receiving portion 736 of the cover 340. In an alternative embodiment, the interior portion of the dispensing unit 140 may rotate clockwise or counterclockwise depending on whether distribution of the contents is permitted or not. For example, when the distribution of the contents is authorized, the interior portion may rotate until the receiving portion 736 is no longer aligned with the gap between the ends of the interior portion 242. The interior portion 242 may act as a gate restricting or preventing the flow of the internal contents to the exit path.

In order to provide rotation, the interior portion 242 may be equipped with a drive shaft or other means for rotating itself. In one embodiment, the interior portion may include a gear 701 interconnected with a second gear 510. In one embodiment, the second gear 510 may be placed in communication with a motor 234a or in an alternative embodiment, the second gear 510 may be placed in communication with the external gears 332 which may be controlled by motor 234b. When the motor initiates or the external gear rotates, the second gear 510 may also rotate thus turning the drive shaft which may be inserted through the interior dispensing unit 242. In an alternative embodiment, a motor 234a may directly receive a drive shaft connected to the interior portion 242 and upon initiation by an administrative user to distribute the contents of the apparatus, the motor may begin rotating interior dispenser portion 242 accordingly for example by rotating gears 510 communicating with the dispensing unit gear 701.

The lower dispensing portion 240 may be may be any shape capable of receiving the interior portion. In one embodiment, the lower portion of the dispensing unit may be any shape capable of containing or holding the dispensed contents of the access compartment. The shape and design of the lower portion 240 may depend on the dosage form being administered. For example in an embodiment wherein a solid dosage form is being administered, the lower portion may be a plate or bowl shape. In an alternative embodiment wherein the dosage form is a liquid dosage form, a the lower portion 240 may be a sealed liquid holding container. In the case of a gaseous or vapor filled contents, the lower portion may be designed to prevent leakages of the gas or may include an inhaler type mechanism or a nebulizer.

Additional embodiments of the lower portion 240 may include slots or notches 351 similar to the ones that may be present in the cover 340. The slots or notches may line up with the cover portion 340, allowing the ridges 350 of the apparatus body 110 to pass through. Accordingly, when the cover and lower portion have been threaded with the ridges, movement of the cover and lower portion may be prevented allowing for the interior portion to move in accordance with user input or preprogrammed instructions. In the exemplary embodiment, the interior portion may perform the rotational work and displace the contents from the lower portion of the dispensing unit 140 to the exit path 107, while the cover and the lower portion remain statically fixed.

Embodiments of a lower dispensing portion 240 designed to include a liquid dispensing mechanism may include one or a plurality of doors, hatches, slides, ports, caps, covers, flaps, lids, closures, or other mechanism which only opens to dispense a controlled substance according to the prescribed dosage and schedule. A liquid dispensing lower portion may also include a liquid dispensing mechanism such as a sensor which controls the amount of liquid controlled substance dispensed at one time. Embodiments of a sensor may include a flow meter, a volume sensor, a scale, or any other device which can detect the amount of liquid dispensed. Embodiments including gaseous, vaporous, or vapor-resultant dispensing mechanisms may be configured to render the controlled substance for prescribed use in a gaseous or vaporous form.

In an alternative embodiment of a liquid dispensing mechanism two doors may be separated by a liquid retrieval chamber. The liquid dispensing mechanism may be formed so as to not allow both doors to be open at the same time thus preventing tampering by liquid or other attempts at unscheduled, unauthorized removal of the controlled substance. Embodiments of a liquid dispensing mechanism may be waterproof, moisture-tight, and vapor-tight. Those skilled in the art should appreciate that there may be other embodiments of a liquid dispensing mechanism.

Testing was performed to determine the efficiency one embodiment of the apparatus 100. The tested embodiment was proven to be 97% accurate. These test results were obtained by feeding 50 pills through the device nine (9) times and counting the number of failures. In the testing, a failure was identified as multiple pills being dispensed or a pill being dispensed but the exit path failing to deliver the pill to the user. An acceptable dispensing was identified as a single pill being dispensed either without assistance, or requiring the user to shake the device to help the wheels interface with the pills.

While this disclosure has been described in conjunction with the specific embodiments outlined above, it is evident that many alternatives, modifications and variations will be apparent to those skilled in the art. Accordingly, the preferred embodiments of the present disclosure as set forth above are intended to be illustrative, not limiting. Various changes may be made without departing from the spirit and scope of the invention, as required by the following claims. The claims provide the scope of the coverage of the invention and should not be limited to the specific examples provided herein.

What is claimed is:

1. A tamper-resistant drug receiving, regulating and dispensing apparatus comprising:
   a tamper-resistant canister including at least one access compartment, at least one regulating unit having an entrance thereto, at least one variable insert that controls the amount of contents being dispensed from the at least one regulating unit by restricting or expanding the entrance to the at least one regulating unit, wherein the at least one variable insert is attached to an inner surface of the at least one access compartment, and a locking mechanism;
   a controller operably in communication with the locking mechanism and the at least one regulating unit, the controller configured to at least control the locking mechanism and the at least one regulating unit; and
   a communication component operably in communication with the controller, the communication component configured to receive one or more instructions from a device external to the tamper-resistant drug receiving, regulating and dispensing apparatus and automatically and without user interaction implement the one or more instructions according to a protocol governing operability of the apparatus, the protocol being configured to identify when drugs are to be dispensed by the apparatus, wherein implementing the one or more instructions causes the controller to dispense a drug at the at least one regulating unit.

2. The apparatus of claim 1 further comprising at least one of a display and a user interface that may be accessed by a facial scan, retinal scan or touch screen hand gestures.

3. The apparatus of claim 2 wherein the at least one of the display and the user interface is a touch screen display.

4. The apparatus of claim 1 wherein the communication component is configured to enable wireless communication.

5. The apparatus of claim 1 wherein the controller includes a governing protocol associated with a programmable timer.

6. The apparatus of claim 1 wherein the at least one access compartment contains a drug having a dosage form selected from the group consisting of: a pill, a table, a capsule, a solution, a suspension, an emulsion, an aerosol, an elixir, a patch, a cream, a lotion, and ointment, a gel, an inhalant, a lozenge, a wafer, and combinations thereof.

7. The apparatus of claim 1 wherein there are at least two access compartments.

8. The apparatus of claim 2 wherein the display presents user information.

9. The apparatus of claim 8 wherein user information includes at least one of identifying patient information, prescribed drugs, drug dosage form, drug dosage amount, patient allergies, drug side effects, drug contraindications, known drug interactions, drug dosing information, prescriber's instructions, and combinations thereof.

10. The apparatus of claim 1 wherein the apparatus is sterilizable.

11. The apparatus of claim 1 wherein the tamper-resistant canister is at least one of pre-sterilized and disposable.

12. A method for securing and controlling the dispensing of drugs contained in a tamper resistant apparatus, the method comprising the steps of:
   providing a tamper-resistant apparatus having a removable cover, a controller, at least one regulating unit having an entrance thereto, at least one variable insert that controls the amount of contents being dispensed from the regulating unit by restricting or expanding the entrance to the regulating unit, wherein the at least one variable insert is attached to an inner surface of an access compartment, and an apparatus body, wherein a portion of the apparatus body is configured to receive and retain one or more drugs;
   engaging a locking mechanism to prevent the separation of the apparatus cover from the apparatus body;
   programming the controller with a security input to control the operation of the locking mechanism;
   programming the controller to dispense the one or more drugs within the portion of the apparatus body at a controlled rate; and
   communicating activity of the apparatus body to an external administrative user.

13. The method of claim 12 wherein the step of engaging a locking mechanism includes rotating the locking mechanism wherein upon rotation at least one locking pin extends through a bore capable of accepting the locking pin.

14. The method of claim 12 wherein the step of programming the controller includes syncing a timer.

15. The method of claim 12 wherein the step of communicating activity includes transmitting apparatus information via a communication component.

16. The method of claim 15 wherein the step of transmitting occurs wirelessly.

17. The method of claim 15 wherein the step of transmitting is facilitated by communication cables.

18. The method of claim 12 further comprising an additional step of sterilizing the tamper-resistant apparatus.

19. The method of claim 18 wherein the step of sterilizing includes replacing the body having a portion thereof configured to receive and retain drugs with a pre-sterilized disposable body.

20. An apparatus for securely dispensing drugs at a controlled rate, the apparatus comprising:
   a tamper-resistant canister, wherein the tamper-resistant canister is comprised of at least two portions, the at least two portions being movable with respect to each other to facilitate access within the canister;
   a communications component, within the tamper-resistant canister, the communications component configured to receive one or more instructions from a source external to the tamper-resistant canister;
   a control unit, within the tamper-resistant canister, the control unit configured to process the one or more instructions received by the communications component and automatically and without user interaction implement one of more actions based on the processed one or more instructions according to a protocol governing operability of the apparatus, the protocol being configured to identify when drugs are to be dispensed by the apparatus;
   an access compartment configured to facilitate reception of one or more drugs within the tamper-resistant canister when the compartment is unlocked, thereby permitting controlled movement of the two movable portions of the tamper-resistant canister and access into the tamper-resistant canister;
   a regulating unit in operable communication with the access compartment and the control unit, the regulating unit configured to regulate a size or an amount of the one or more drugs to be dispensed;
   at least one variable insert that controls the amount of contents being dispensed from the regulating unit by restricting or expanding an entrance to the regulating unit, wherein the at least one variable insert is attached to an inner surface of the access compartment; and
   a dispensing unit configured to dispense the one or more drugs according to at least one of the one or more instructions provided by the source external to the tamper-resistant canister and processed by the control unit.

21. The apparatus of claim 20, wherein the apparatus includes a battery within the tamper-resistant canister, the battery configured to power mechanical and electrical components of the apparatus.

22. The apparatus of claim 20, wherein the control unit includes sufficient memory to hold prescription and patient information, the memory configured so as to be loaded with dosing, scheduling and prescription information in a manner that retains the prescription, dosing schedule and patient information even when there is a loss of power.

23. The apparatus of claim 20, wherein the tamper-resistant canister is sterilizable.

24. The apparatus of claim 20, wherein the tamper-resistant canister is at least one of pre-sterilized and disposable.

25. The apparatus of claim 1, wherein the tamper-resistant canister has a tensile strength greater than 40 MPa.

26. The apparatus of claim 1, wherein the tamper-resistant canister has an impact strength greater than 5 ft-lb/in.

27. The apparatus of claim 1, wherein the tamper-resistant canister has a flexural strength greater than 59 MPa.

28. The apparatus of claim 1, wherein the tamper-resistant canister has a maximum vertical load strength to mass ratio of 32,000 Newtons per kilogram.

29. The apparatus of claim 1, wherein the at least one variable insert is attached to the at least one access compartment with a clip.

* * * * *